(12) United States Patent
Brady et al.

(10) Patent No.: US 7,052,865 B1
(45) Date of Patent: May 30, 2006

(54) IDENTIFICATION OF GENES HAVING A ROLE IN THE PRESENTATION OF DIABETIC NEPHROPATHY

(75) Inventors: Hugh Redmond Brady, Killiney (IE); Catherine Mary Godson, Dublin (IE); Finian Mary Martin, Dublin (IE); Ruth Anne McMahon, Dublin (IE); Madeline Anne Murphy, Dublin (IE)

(73) Assignees: University College Dublin, National University of Ireland, Dublin, Dublin (IE); Hibergen Limited, Bray (IE)

( * ) Notice: Subject to any disclaimer, the term of this patent is extended or adjusted under 35 U.S.C. 154(b) by 0 days.

(21) Appl. No.: 09/914,191

(22) PCT Filed: Feb. 28, 2000

(86) PCT No.: PCT/IE00/00026

§ 371 (c)(1),
(2), (4) Date: Aug. 24, 2001

(87) PCT Pub. No.: WO00/50637

PCT Pub. Date: Aug. 31, 2000

(30) Foreign Application Priority Data

Feb. 26, 1999 (IE) ................................................ 990157

(51) Int. Cl.
*C12Q 1/00* (2006.01)
*C12Q 1/02* (2006.01)
*C07H 21/04* (2006.01)

(52) U.S. Cl. ................................ 435/29; 435/4; 435/6; 536/2.35

(58) Field of Classification Search ...................... 435/4, 435/6, 29; 536/23.5
See application file for complete search history.

(56) References Cited

PUBLICATIONS

Murphy et al. Gene expression in cultured human mesangial cells in response to extracellular glucose as assessed by suppressive subtractive hybridization. J. Am. Soc. Nephrol. (Sep., 1998) vol. 9, 673A.*
Girard J. Mechanisms by which carbohydrates regulate expression of genes for glycolytic □□and lipogenic enzymes.□□Annu Rev Nutr. 1997;17:325–52.*
Riser et al. Mechanical strain– and high glucose–induced alterations in mesangial cell collagen metabolism: role of TGF–beta. J Am Soc Nephrol. May 1998;9(5):827–36.*
Holmes et al., Biochemical and Biophysical Research Communications, vol. 238, No.1, pp. 179–184 (1997).
Myers, Database EMSTS Online, Accesion No. G38490 xP002143063 (1998).
Hillier et al., Database EMEST Online, Accesion No. AA071138, XP002143064 (1996).
Murphy et al., Journal of Biological Chemistry, vol. 274, NO. 9, pp. 5830–4 (1999).
Sugano et al., Database EMHUM Online, Accesion No. AK000553, XP002143065 (2000).
Hillman et al., Database GENESEQ Online, Accession No. Z52443 (WO–A–9957144), XP002143066 (2000).
Hillier et al., Databased EMEST Online, Accession No. N52279, XP002143067 (1996).
Ryseck et al., Cell Growth & Differentiation, vol. 2 (1991) pp. 225–233.
Ozaki et al., Cancer Research, vol. 55 (1995) pp. 895–900.
Topol et al., Molecular and Cellular Biology, vol. 17, No. 8 (1997) pp. 4801–4810.
Ghosh–Choudhury et al., Biochemical and Biophysical Research Communications, vol. 258 (1999) pp. 490–496.
Ghosh–Choundhury et al., J. of Biological Chemistry, vol. 274, No. 16 (1999) pp. 10897–10902.
Brenner et al., New England Journal of Medicine, vol. 307, No. 11 (1982) pp. 652–659.
Stewart et al., Clin. Genet., vol. 49 (1996) pp. 152–155.
Guffanti et al., TIG, vol. 14, No. 7 (1998) p. 293.
Altschul et al., Nucleic Acids Research, vol. 25, No. 17 (1997) pp. 3389–3402.
Ito et al., Kidney Int., vol. 53 (1998) pp. 853–861.
Bradham et al., J. of Cell Biology, vol. 114, No. 6 (1991) pp. 1285–1294.
Bork, FEBS Letts., vol. 327, No. 2 (1993) pp. 125–130.
Kreisberg et al., Kidney Int., vol. 43 (1993) pp. 109–113.
Sohn et al., BioEssays, vol. 16, No. 7 (1994) pp. 465–472.
Zhou et al., Kidney Int., vol. 51 (1997) pp. 1797–1808.
Zhou et al., Lab. Invest., vol. 73, No. 3 (1995) pp. 372–383.
Zatz et al., Proc. Natl. Acad. Sci., vol. 82 (1985) pp. 5963–5967.
Denton et al., Am. J. Physiol., vol. 261 (1991) pp. F1071–F1079.
Brady et al., Kidney Int., vol. 42 (1992) pp. 480–487.
Zuniga et al., Nature, vol. 401 (1999) pp. 598–602.
Hsu et al., Molecular Cell, vol. 1 (1998) pp. 673–683.
Sharma et al., Diabetes, vol. 45 (1996) pp. 522–530.
Park et al., Diabetes, vol. 46 (1997) pp. 473–480.
Sharma et al., Diabetes, vol. 44 (1995) pp. 1139–1146.

(Continued)

*Primary Examiner*—David Guzo
*Assistant Examiner*—Daniel M. Sullivan
(74) *Attorney, Agent, or Firm*—Birch, Stewart, Kolasch & Birch, LLP

(57) ABSTRACT

A method for identifying a gene having a role in the presentation of diabetic nephropathy comprises culturing mesangial cells in the presence of a concentration of glucose sufficient to induce differential expression, especially up-regulation, of a gene susceptible to such differential expression and identifying the gene so induced. The cells are also optionally subjected to mechanical strain and/or TGF-β1 can be added to the culture medium. The differentially expressed genes can be identified by suppression subtractive hybridisation. The method has resulted in the Identification of novel genes which play a role in the presentation of diabetic nephropathy. The genes can be used as diagnostic markers for diabetic nephropathy and as the basis of drug development programmes.

7 Claims, 24 Drawing Sheets

OTHER PUBLICATIONS

Goldfarb et al., *Diabetes*, vol. 40 (1991) pp. 465–471.
Cohen et al., *Kidney Int.*, vol. 45 (1994) pp. 475–484.
Brownlee et al., *Annals of Internal Medicine*, vol. 101, No. 4 (1984) pp. 527–537.
Derubertis et al., *Diabetes*, vol. 43 (1994) pp. 1–8.
Hubank et al., *Nucleic Acids Research*, vol. 22, No. 25 (1994) pp. 5640–5648.
Liang et al., *Science*, vol. 257 (1992) pp. 967–971.
Gurskaya et al., *Analytical Biochemistry*, vol. 240 (1996) pp. 90–97.
Ayo et al., *Am. J. Physiol.*, vol. 260 (1991) pp. F185–F191.
Wahab et al., *Biochem. J.*, vol. 316 (1996) pp. 985–992.
Ayo et al., *Am. J. Pathol.*, vol. 136, No. 6 (1990) pp. 1339–1348.
Yazaki et al., *Anticancer Research*, vol. 18 (1998) pp. 2339–2344.

* cited by examiner

```
rat:   1     atctccacccgGgttaccaatgacaatacTttctgcagGctggagaagcagagTcgTctc  60
             ||||||||||| ||||||||||||||||| ||||||||  ||||||||||||| || |||
mouse: 783   atctccacccgagttaccaatgacaataccttctgcagactggagaagcagagccgcctc  842 rat:  61     tgcatggtcaggccctgTgaagctgacctAgaggaaaacattaagaagggcaaaaagtgc  120
             ||||||||||||||||| |||||||||| |||||||||| ||||||||||||||||||||
mouse: 843   tgcatggtcaggccctgcgaagctgacctggaggaaaacattaagaagggcaaaaagtgc  902 rat: 121     atccggacGcctaaaatTgccaagcctgtcaagtttgagctttctggctgcaccagtgtg  180
             |||||||| |||||||| ||||||||||||||||||||||||||||||||||||||||||
mouse: 903   atccggacacctaaaatcgccaagcctgtcaagtttgagctttctggctgcaccagtgtg  962 rat: 181     aagacCtacCgggctaagttctgTggggtgtgcacGgacggccgctgctgcacaccgcac  240
             ||||| ||| ||||||||||||| |||||||||| |||||||||||||||||||||||||
mouse: 963   aagacatacagggctaagttctgcggggtgtgcacagacggccgctgctgcacaccgcac  1022 rat: 241     agaaccaccacActgccggtggagttcaaGtgccccCatggcgaAatcatgaaaaagaac  300
             ||||||||||| ||||| ||||||||||| |||||| |||||||| |||||||||||| |
mouse: 1023  agaaccaccactctgccagtggagttcaaatgccccgatggcgagatcatgaaaaagaat  1082 rat: 301     atgatgttcatcaagacctgtgcctgccattacaactgtcc  341    (SEQ ID NO: 29)
             |||||||||||||||||||||||||||||||||||||||||
mouse: 1083  atgatgttcatcaagacctgtgcctgccattacaactgtcc  112    (SEQ ID NO: 30)
```

Fig. 4 rat:    1  ISTRVTNDNTFCRLEKQSRLCMVRPCEADLEENIKKGKKCIRTPKIAKPVKFELSGCTSV 180
mouse: 216 ISTRVTNDNTFCRLEKQSRLCMVRPCEADLEENIKKGKKCIRTPKIAKPVKFELSGCTSV 275 rat:   181 KTYRAKFCGVCTDGRCCTPHRTTTLPVEFKCPHGEIMKKNMMFIKTCACHYNC 339   (SEQ ID NO: 31)
mouse: 276 KTYRAKFCGVCTDGRCCTPHRTTTLPVEFKCPDGEIMKKNMMFIKTCACHYNC 328   (SEQ ID NO: 32)

Fig. 5

```
   1  GCGGCCGCACTCAGCGCCACGCGTCGAAAGCGCAGGCCCCGAGGACCCGCCGCACTGACAGTATGAGCCGCACAG
                                                                      M  S  R  T  A
  76  CCTACACGGTGGGAGCCCTGCTTCTCCTCTTGGGGACCCTGCTGCCGGCTGCTGAAGGGAAAAAGAAAGGGTCCC
       Y  T  V  G  A  L  L  L  L  L  G  T  L  L  P  A  A  E  G  K  K  K  G  S  Q
 151  AAGGTGCCATCCCCCCGCCAGACAAGGCCCAGCACAATGACTCAGAGCAGACTCAGTCGCCCCAGCAGCCTGGCT
       G  A  I  P  P  P  D  K  A  Q  H  N  D  S  E  Q  T  Q  S  P  Q  Q  P  G  S
 226  CCAGGAACCGGGGCGGGGCCAAGGGCGGGGCACTGCCATGCCCGGGGAGGAGGTGCTGGAGTCCAGCCAAGAGG
       R  N  R  G  R  G  Q  G  R  G  T  A  M  P  G  E  E  V  L  E  S  S  Q  E  A
 301  CCCTGCATGTGACGGAGCGCAAATACCTGAAGCGAGACTGGTGCAAAACCCAGCCGCTTAAGCAGACCATCCACG
       L  H  V  T  E  R  K  Y  L  K  R  D  W  C  K  T  Q  P  L  K  Q  T  I  H  E
 376  AGGAAGGCTGCAACAGTCGCACCATCATCAACCGCTTCTGTTACGGCCAGTGCAACTCTTTCTACATCCCCAGGC
       E  G  C  N  S  R  T  I  I  N  R  F  C  Y  G  Q  C  N  S  F  Y  I  P  R  H
 451  ACATCCGGAAGGAGGAAGGTTCCTTTCAGTCCTGCTCCTTCTGCAAGCCCAAGAAATTCACTACCATGATGGTCA
       I  R  K  E  E  G  S  F  Q  S  C  S  F  C  K  P  K  K  F  T  T  M  M  V  T
 526  CACTCAACTGCCCTGAACTACAGCCACCTACCAAGAAGAAGAGAGTCACACGTGTGAAGCAGTGTCGTTGCATAT
       L  N  C  P  E  L  Q  P  P  T  K  K  K  R  V  T  R  V  K  Q  C  R  C  I  S
 601  CCATCGATTTGGATTAAGCCAAATCCAGGTGCACCCAGCATGTCCTAGGAATGCAGCCCCAGGAAGTCCCAGACC
       I  D  L  D
 676  TAAAACAACCAGATTCTTACTTGGCTTAAACCTAGAGGCCAGAAGAACCCCCAGCTGCCTCCTGGCAGGAGCCTG
 751  CTTGTGCGTAGTTCGTGTGCATGAGTGTGGATGGGTGCCTGTGGGTGTTTTTAGACACCAGAGAAAACACAGTCT
 826  CTGCTAGAGAGCACTCCCTATTTTGTAAACATATCTGCTTTAATGGGGATGTACCAGAAACCCACCTCACCCCGG
 901  CTCACATCTAAAGGGGCGGGGCCGTGGTCTGGTTCTGACTTTGTGTTTTTGTGCCCTCCTGGGGACCAGAATCTC
 976  CTTTCGGAATGAATGTTCATGGAAGAGGCTCCTCTGAGGGCAAGAGACCTGTTTTAGTGCTGCATTCGACATGGA
1051  AAAGTCCTTTTAACCTGTGCTTGCATCCTCCTTTCCTCCTCCTCCTCACAATCCATCTCTTCTTAAGTTGATAGT
1126  GACTATGTCAGTCTAATCTCTTGTTTGCCAAGGTTCCTAAATTAATTCACTTAACCATGATGCAAATGTTTTTCA
1201  TTTTGTGAAGACCCTCCAGACTCTGGGAGAGGCTGGTGTGGGCAAGGACAAGCAGGATAGTGGAGTGAGAAAGGG
1276  AGGGTGGAGGGTGAGGCCAAATCAGGTCCAGCAAAAGTCAGTAGGGACATTGCAGAAGCTTGAAAGGCCAATACC
1351  AGAACACAGGCTGATGCTTCTGAGAAAGTCTTTTCCTAGTATTTAACAGAACCCAAGTGAACAGAGGAGAAATGA
1426  GATTGCCAGAAAGTGATTAACTTTGGCCGTTGCAATCTGCTCAAACCTAACACCAAACTGAAAACATAAATACTG
1501  ACCACTCCTATGTTCGGACCCAAGCAAGTTAGCTAAACCAAACCAACTCCTCTGCTTTGTCCCTCAGGTGGAAAA
1576  GAGAGGTAGTTTAGAACTCTCTGCATAGGGGTGGGAATTAATCAAAAACCKCAGAGGCTGAAATTCCTAATACCT
1651  TTCCTTTATCGTGGTTATAGTCAGCTCATTTCCATTCCACTATTTCCCATAATGCTTCTGAGAGCCACTAACTTG
1726  ATTGATAAAGATCCTGCCTCTGCTGAGTGTACCTGACAGTAAGTCTAAAGATGARAGAGTTTAGGGACTACTCTG
1801  TTTTAGCAAGARATATTKTGGGGTCTTTTTGTTTTAACTATTGTCAGGAGATTGGGCTARAGAGAAGACGACGA
1876  GAGTAAGGaAATAAAGGGRATTGCCTCTGGCTAGAGAGTAAGTTAGGTGTTAATACCTGGTAGAAATGTAAGGGA
1951  TATGACCTCCCTTTCTTTATGTGCTCACTGAGGATCTGAGGGGACCCTGTTAGGAGAGCATAGCATCATGATGTA
2026  TTAGCTGTTCATCTGCTACTGGTTGGATGGACATAACTATTGTAACTATTCAGTATTTACTGGTAGGCACTGTCC
2101  TCTGATTAAACTTGGCCTACTGGCAATGGCTACTTAGGATTGATCTAAGGGCCAAAGTGCAGGGTGGGTGAACTT
2176  TATTGTACTTTGGATTTGGTTAACCTGTTTCTTCAAGCCTGAGGTTTTATATACAAACTCCCTGAATACTCTTT
2251  TTGCCTTGTATCTTCTCAGCCTCCTAGCCAAGTCCTATGTAATATGGAAAACAAACACTGCAGACTTGAGATTCA
2326  GTTGCCGATCAAGGCTCTGGCATTCAGAGAACCCTTGCAACTCGAGAAGCTGTTTTTATTTCGTTTTTGTTTTGA
2401  TCCAGTGCTCTCCCATCTAACAACTAAACAGGAGCCATTTCAAGGCGGGAGATATTTTAAACACCCAAAATGTTG
2476  GGTCTGATTTTCAAACTTTTAAACTCACTACTGATGATTCTCACGCTAGGCGAATTTGTCCAAACACATAGTGTG
2551  TGTGTTTTGTATACACTGTATGACCCCCACCCCAAATCTTTGTATTGTCCACATTCTCCAACATTTCACAGAG
2626  TGGATTTAATTAAGCACACAAATGCTAAGGCAGAATTTTGAGGGTGGGAGAGAAGAAAAGGGAAAGAAGCTGAAA
2701  ATGTAAAACCACACCAGGGAGGAAAAATGACATTCAGAACCAGCAAACACTGAATTTCTCTTGTTGTTTTAACTC
2776  TGCCACAAGAATGCAATTTCGTTAATGGAGATGACTTAAGTTGGCAGCAGTAATCTTCTTTTAGGAGCTTGTACC
2851  ACAGTCTTGCACATAAGTGCAGATTTGGCTCAAGTAAAGAGAATTTCCTCAACACTAACTTCACTGGGATAATCA
2926  GCAGCGTAACTACCCTAAAAGCCATACTAGCCAAAGAGGGAAATATCTGTTCTTCTTACTGTGCCTATATTAA
3001  GACTAGTACAAATGTGGTGTGTCTTCCAACTTTCATTGAAAATGCCATATCTATACCATATTTTATTCGAGTCAC
3076  TGATGATGTAATGATATATTTTTTCATTATTATAGTAGAATATTTTTATGGCAAGATATTTGTGGTCTTGATCAT
3151  ACCTATTAAAATAATGCCAAACACCAAATATGAATTTTATGATGTACACTTTGTGCTTGGCATTAAAAGAAAAAA
3226  ACACACATCCTGGAAGTCTGTAAGTTGTTTTTTGTTACTGTAGGTCTTCAAAGTTAAGAGTGTAAGTGAAAAATC
3301  TGGAGGAGAGGATAATTTCCACTGTGTGGAATGTGAATAGTTAAATGAAAAGTTATGGTTATTTAATGTAATTAT
3376  TACTTCAAATCCTTTGGTCACTGTGATTTCAAGCATGTTTTCTTTTTCTCCTTTATATGACTTTCTCTGAGTTGG
3451  GCAAAGAAGAAGCTGACACACCGTATGTTGTTAGAGTCTTTTATCTGGTCAGGGGAAACAAAATCTTGACCCAGC
3526  TGAACATGTCTTCCTGAGTCAGTGCCTGAATCTTATTTTTAAATTGAATGTTCCTTAAAGGTTAACATTTCTA
3601  AAGCAATATTAAGAAAGACTTTAAATGTTATTTGGAAGACTTACGATGCATGTATACAAACGAATAGCAGATAA
3676  TGATGACTAGTTCACACATAAAGTCCTTTTAAGGAGAAAATCTAAAATGAAAAGTGGATAAACAGAACATTTATA
3751  AGTGATCAGTTAATGCCTAAGAGTGAAAGTAGTTCTATTGACATTCCTCAAGATATTTAATATCAACTGCATTAT
3826  GTATTATGTCTGCTTAAATCATTTAAAAACGGCAAAGAATTTATATAGACTATGAGGTACCTTGCTGTGTAGGAGG
3901  ATGAAAGGGGACTTGATAGTCTCATAAAACTAATTTGGCTTCAAGTTTCATGAATCTGTAACTAGAATTTAATTT
3976  TCACCCCAATAATGTTCTATATAGCCTTTGCTAAAGAGCAACTAATAAATTAAACCTATTCTTTCAAAAAAAAA
```

(SEQ ID NO: 33)

Fig. 15

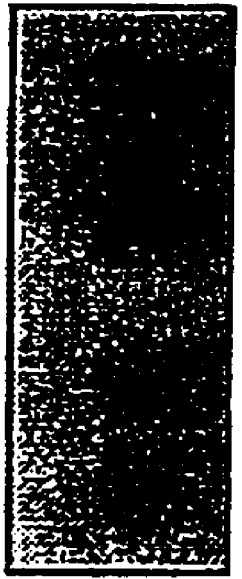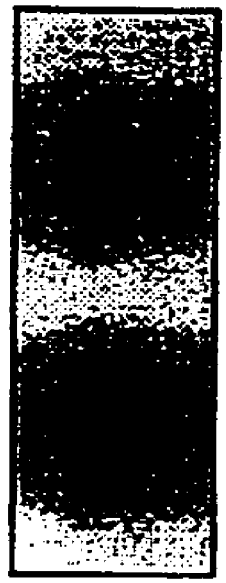
FIG. 20

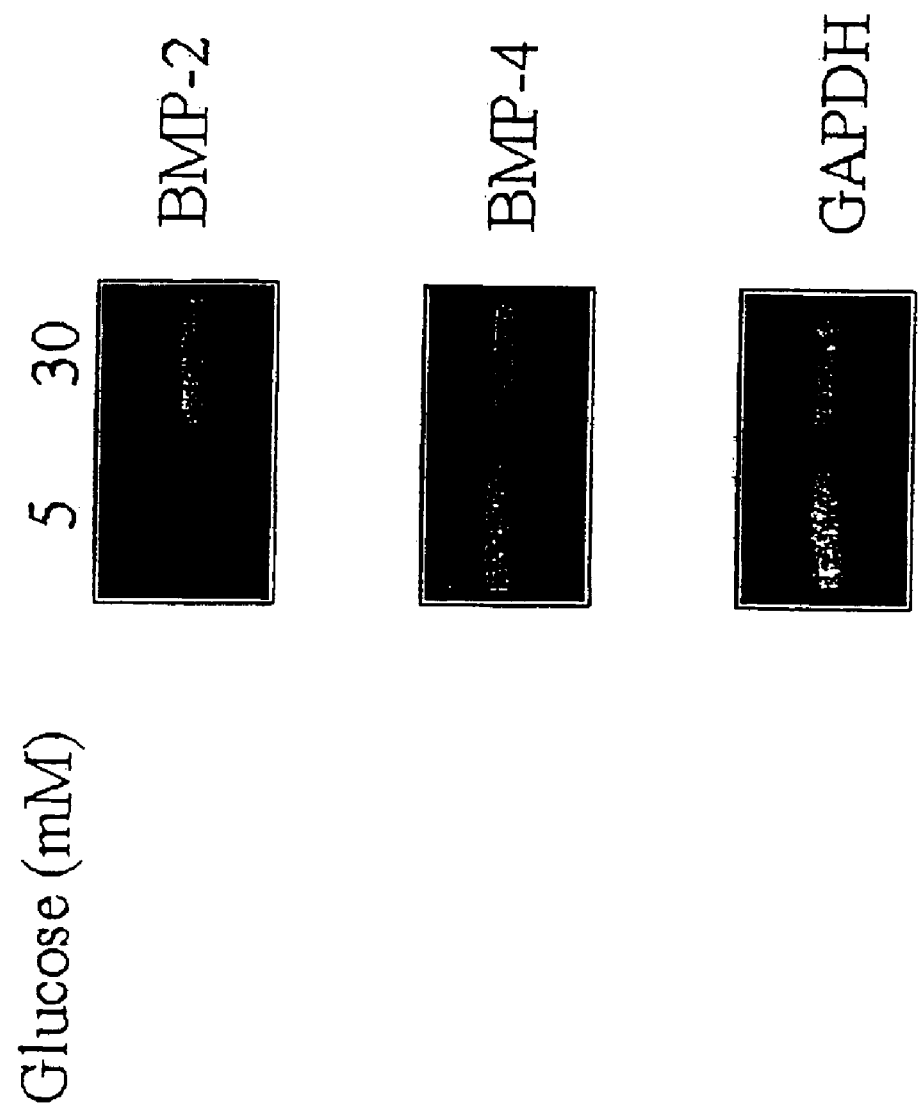

SEQUENCE LISTING

<160> NUMBER OF SEQ ID NOS: 33

<210> SEQ ID NO 1
<211> LENGTH: 598
<212> TYPE: DNA

<213> ORGANISM: Homo sapiens
<220> FEATURE:
<221> NAME/KEY: Unsure
<222> LOCATION: (1)..(598)
<223> OTHER INFORMATION: any n =a,c,g,t any unknown or other

<400> SEQUENCE: 1

```
ttggaatagt tcttgcttta taaaaatagt actgcgatta aaaaaaaagc acttctgcca    60
aaggaaccat gttccaacac cgcaaacaag gtgttctgct taaacagagt aagatacacc   120
accccatcc atcccttcct tccctgttcc cctcccaact tgagttgtgt cattcgcacc   180
agtgtcctgg gtggtaggga tgctacagcc acctaaggca aggagccctg ggaggtggga   240
gggcttgcat ggttaagcac accagaactg aagcgcaaaa gggtcagctg tcttcatcta   300
gaatctctgg atgttccttc cagaaagcat ccccgatgat atcgcagtgc aagggcactg   360
gctttgtcct ggtccgggtc actgccatct ttttccttc catttctgtt ggcagcttaa   420
tttcttttgt catcacttca tccaccttct gccatatcaa cacagtccct ttcctataca   480
tcggcagctc attattatag ttgatgttga attcagaaaa caaaatctca ttcttgtctg   540
ctgnaagagt tccctgtaat ctcccttggg cttgtactgg tgttagtcca gattgttg    598
```

<210> SEQ ID NO 2
<211> LENGTH: 761
<212> TYPE: DNA
<213> ORGANISM: Homo sapiens
<220> FEATURE:
<221> NAME/KEY: Unsure
<222> LOCATION: (1)..(761)
<223> OTHER INFORMATION: any n =a,c,g,t any unknown or other

<400> SEQUENCE: 2

```
ggtcctttaa agtctggttg ctgggataca ccacgactct tccggtcaaa gcctggggga    60
tacagaaggg gctrgtcctc aaagtaatcc cgccaataaa acayatagct ggaggcaaac   120
tgggaggyca cgtgagtcat gaactttact ggctcttctt ttaaaccaat tggttttccg   180
cttgwacaca aagctgtact catcactctg tccataacgc gatcacaata tcctctagtt   240
cttccatcac agtctgcgca catttggtca tcagctggag agcacggctg tcattgggtt   300
ttgcaaagtt gtgcttctca gcaaaccgat ggaaattccg gccgtccagc cgnactacca   360
cccagcagtg tgccaggcag gtgtcgtcag cctcgaagtc cctcacgtac tcgaacttgc   420
tttttgccat ggtcgccccc aatctccagg accgtctcag agtgatgaa atggtggcca   480
aggaatcgtg aaccttaact ttacaggcgc cccacattct acacgcggaa aggaaagggc   540
cagatagccc cgccccggaa gtgttctctt cgtggctact ctagccgtag ggcggtcata   600
gtctctctcg sctctccctg kagttcttaa mcyyccaggg aaaraggatg gaggtttagg   660
ttcctccgtt agcaccttcc acgcttgctt cttcctcctc ccggtctgcg gcaaatcagt   720
ctcacgaggt ttttaaaaat tattttttat ctgctggcct t                      761
```

<210> SEQ ID NO 3
<211> LENGTH: 393
<212> TYPE: DNA
<213> ORGANISM: Homo sapiens
<220> FEATURE:
<221> NAME/KEY: Unsure
<222> LOCATION: (1)..(393)
<223> OTHER INFORMATION: any n =a,c,g,t any unknown or other

<400> SEQUENCE: 3

```
atgacacaaa tattaggatt ttattttttac tattatccac cagcaacaag atatcaaaca    60
```

```
ctggttctgt gattatttaa tggtgaaaaa gttgaataaa tcaatttagt atacccatat      120
gttggaatat tgagtccatt tttcttttaa aaatcacact ttggaataat tgatgatact      180
ggcaaatgct caagctgagt ggaaaaatat ataaacattg tataggcgaa taattccaat      240
cttgtgcatt ccctgtgtaa acctacatac acaaaaagaa aaaagactga aaggaaccat      300
ccacaatgct tgatcggga aagacggaga acaaagtgt taattttctt aactatagtt        360
ttnggtgtat tccagatttt ctacaagtta ata                                   393

<210> SEQ ID NO 4
<211> LENGTH: 435
<212> TYPE: DNA
<213> ORGANISM: Homo sapiens

<400> SEQUENCE: 4
gtactttgga tttggttaac ctgttttctt caagcctgag gttttatata caaactccct      60
gaatactctt tttgccttgt atcttctcag cctcctagcc aagtcctatg taatatggaa      120
aacaaacact gcagacttga gattcagttg ccgatcaagg ctctggcatt cagagaaccc      180
ttgcaactcg agaagctgtt tttatttcgt ttttgttttg atccagtgct ctcccatcta      240
acaactaaac aggagccatt tcaaggcggg agatatttta aacacccaaa atggttgggt      300
ctgattttca aacttttaaa attcactact gatgattctg cacgctaagg cgaatttggt      360
ccaaacacat aagtgtgtgt gttttgtata cactgtatga ccccaccca aatctttgta       420 ttgtccacat tctcc                                                       435

<210> SEQ ID NO 5
<211> LENGTH: 273
<212> TYPE: DNA
<213> ORGANISM: Homo sapiens
<220> FEATURE:
<221> NAME/KEY: Unsure
<222> LOCATION: (1)..(273)
<223> OTHER INFORMATION: any n =a,c,g,t any unknown or other

<400> SEQUENCE: 5
agaagcaatt taggaanccn acagnaaana aatgctgttt tataggagag aaaacacggc      60
acaccaaggt taagtagttt gtagacgatg ttgaataggt tcaggtacag gtcaatgcag      120
tgatgaggaa agcacctang tatacttgac agatagtccc ctttgcttaa cacccaactc      180
ctccaccctg tgcagttttnn cttgtgccag tgatcacagg attcgctgag tgaattacca      240
taattggatt taattcacga aggggatgtt ttc                                   273

<210> SEQ ID NO 6
<211> LENGTH: 309
<212> TYPE: DNA
<213> ORGANISM: Homo sapiens

<400> SEQUENCE: 6
attgatagag gccctgtttc atgacatttc atgagtttca atatgttgtt cagcatgttg      60
tgaggtgact ctcagcccct ttcccactga gatggactgt ggtgatgctg tgagggtgtg      120
actgacacac cttcatgtgc ccaagcatgg gtttgatcac aggtcacatg cagttttttgg    180 catagtaaat gtatcattgt tcttttcctc cctcctaaag gaaacagagg aatccacctg      240
tatgagagtg ccatgtaggg ataaacttaa aggacagatg acacattggt catgttcgtg      300
ataaggaaa                                                              309
```

```
<210> SEQ ID NO 7
<211> LENGTH: 20
<212> TYPE: DNA
<213> ORGANISM: Homo sapiens

<400> SEQUENCE: 7
accacagtcc atgccatcac                                               20

<210> SEQ ID NO 8
<211> LENGTH: 20
<212> TYPE: DNA
<213> ORGANISM: Homo sapiens

<400> SEQUENCE: 8
tccaccaccc tgttgctgta                                               20

<210> SEQ ID NO 9
<211> LENGTH: 20
<212> TYPE: DNA
<213> ORGANISM: Homo sapiens

<400> SEQUENCE: 9
ggtcttcctg gcttaaaggg                                               20

<210> SEQ ID NO 10
<211> LENGTH: 20
<212> TYPE: DNA
<213> ORGANISM: Homo sapiens

<400> SEQUENCE: 10
gctggtcagc cctgtagaag                                               20

<210> SEQ ID NO 11
<211> LENGTH: 20
<212> TYPE: DNA
<213> ORGANISM: Homo sapiens

<400> SEQUENCE: 11
ccaggagttc caggatttca                                               20

<210> SEQ ID NO 12
<211> LENGTH: 20
<212> TYPE: DNA
<213> ORGANISM: Homo sapiens

<400> SEQUENCE: 12
ttttggtccc agaaggacac                                               20

<210> SEQ ID NO 13
<211> LENGTH: 18
<212> TYPE: DNA
<213> ORGANISM: Homo sapiens

<400> SEQUENCE: 13
cgaaatcaca gccagtag                                                 18

<210> SEQ ID NO 14
<211> LENGTH: 18
<212> TYPE: DNA
<213> ORGANISM: Homo sapiens

<400> SEQUENCE: 14
atcacatcca cacggtag                                                 18
```

```
<210> SEQ ID NO 15
<211> LENGTH: 20
<212> TYPE: DNA
<213> ORGANISM: Homo sapiens

<400> SEQUENCE: 15
ctaagacctg tggaatgggc                                                    20

<210> SEQ ID NO 16
<211> LENGTH: 21
<212> TYPE: DNA
<213> ORGANISM: Homo sapiens

<400> SEQUENCE: 16
ctcaaagatg tcattgtccc c                                                  21

<210> SEQ ID NO 17
<211> LENGTH: 20
<212> TYPE: DNA
<213> ORGANISM: Homo sapiens

<400> SEQUENCE: 17
atgagccgca cagcctacac                                                    20

<210> SEQ ID NO 18
<211> LENGTH: 23
<212> TYPE: DNA
<213> ORGANISM: Homo sapiens

<400> SEQUENCE: 18
ttaatccaaa tcgatggata tgc                                                23

<210> SEQ ID NO 19
<211> LENGTH: 21
<212> TYPE: DNA
<213> ORGANISM: Homo sapiens

<400> SEQUENCE: 19
ctcagcctcc tagccaagtc c                                                  21

<210> SEQ ID NO 20
<211> LENGTH: 21
<212> TYPE: DNA
<213> ORGANISM: Homo sapiens

<400> SEQUENCE: 20
gtattgtcca cattctccaa c                                                  21

<210> SEQ ID NO 21
<211> LENGTH: 20
<212> TYPE: DNA
<213> ORGANISM: Homo sapiens

<400> SEQUENCE: 21
atgagccgca cagcctacac                                                    20

<210> SEQ ID NO 22
<211> LENGTH: 21
<212> TYPE: DNA
<213> ORGANISM: Homo sapiens

<400> SEQUENCE: 22
```

```
gtattgtcca cattctccaa c                                                21

<210> SEQ ID NO 23
<211> LENGTH: 20
<212> TYPE: DNA
<213> ORGANISM: Homo sapiens

<400> SEQUENCE: 23
gagagtcaca cgtgtgaagc                                                  20

<210> SEQ ID NO 24
<211> LENGTH: 19
<212> TYPE: DNA
<213> ORGANISM: Homo sapiens

<400> SEQUENCE: 24
aggaggatgc aagcacagg                                                   19

<210> SEQ ID NO 25
<211> LENGTH: 29
<212> TYPE: DNA
<213> ORGANISM: Homo sapiens

<400> SEQUENCE: 25
cgcggatcct gcttcttaga cggactgcg                                        29

<210> SEQ ID NO 26
<211> LENGTH: 20
<212> TYPE: DNA
<213> ORGANISM: Homo sapiens

<400> SEQUENCE: 26
tttgctgtac tagcgacacc                                                  20

<210> SEQ ID NO 27
<211> LENGTH: 18
<212> TYPE: DNA
<213> ORGANISM: Homo sapiens

<400> SEQUENCE: 27
caagatgaac acagctgg                                                    18

<210> SEQ ID NO 28
<211> LENGTH: 18
<212> TYPE: DNA
<213> ORGANISM: Homo sapiens

<400> SEQUENCE: 28
gctcaggata ctcaagac                                                    18

<210> SEQ ID NO 29
<211> LENGTH: 341
<212> TYPE: DNA
<213> ORGANISM: Rattus sp.

<400> SEQUENCE: 29
atctccaccc gggttaccaa tgacaatact ttctgcaggc tggagaagca gagtcgtctc      60
tgcatggtca ggccctgtga agctgaccta gaggaaaaca ttaagaaggg caaaaagtgc     120
atccggacgc ctaaaattgc caagcctgtc aagtttgagc tttctggctg caccagtgtg     180
aagacctacc gggctaagtt ctgtggggtg tgcacggacg gccgctgctg cacaccgcac     240
agaaccacca cactgccggt ggagttcaag tgcccccatg gcgaaatcat gaaaaagaac     300
```

```
atgatgttca tcaagacctg tgcctgccat tacaactgtc c              341
```

<210> SEQ ID NO 30
<211> LENGTH: 341
<212> TYPE: DNA
<213> ORGANISM: Mus sp.

<400> SEQUENCE: 30

```
atctccaccc gagttaccaa tgacaatacc ttctgcagac tggagaagca gagccgcctc    60
tgcatggtca ggccctgcga agctgacctg gaggaaaaca ttaagaaggg caaaaagtgc   120
atccggacac ctaaaatcgc caagcctgtc aagtttgagc tttctggctg caccagtgtg   180
aagacataca gggctaagtt ctgcggggtg tgcacagacg gccgctgctg cacaccgcac   240
agaaccacca ctctgccagt ggagttcaaa tgccccgatg gcgagatcat gaaaaagaat   300
atgatgttca tcaagacctg tgcctgccat tacaactgtc c                      341
```

<210> SEQ ID NO 31
<211> LENGTH: 113
<212> TYPE: PRT
<213> ORGANISM: Rattus sp.

<400> SEQUENCE: 31

```
Ile Ser Thr Arg Val Thr Asn Asp Asn Thr Phe Cys Arg Leu Glu Lys
 1               5                  10                  15

Gln Ser Arg Leu Cys Met Val Arg Pro Cys Glu Ala Asp Leu Glu Glu
            20                  25                  30

Asn Ile Lys Lys Gly Lys Lys Cys Ile Arg Thr Pro Lys Ile Ala Lys
        35                  40                  45

Pro Val Lys Phe Glu Leu Ser Gly Cys Thr Ser Val Lys Thr Tyr Arg
    50                  55                  60

Ala Lys Phe Cys Gly Val Cys Thr Asp Gly Arg Cys Cys Thr Pro His
65                  70                  75                  80

Arg Thr Thr Thr Leu Pro Val Glu Phe Lys Cys Pro His Gly Glu Ile
                85                  90                  95

Met Lys Lys Asn Met Met Phe Ile Lys Thr Cys Ala Cys His Tyr Asn
            100                 105                 110

Cys
```

<210> SEQ ID NO 32
<211> LENGTH: 113
<212> TYPE: PRT
<213> ORGANISM: Mus sp.

<400> SEQUENCE: 32

```
Ile Ser Thr Arg Val Thr Asn Asp Asn Thr Phe Cys Arg Leu Glu Lys
 1               5                  10                  15

Gln Ser Arg Leu Cys Met Val Arg Pro Cys Glu Ala Asp Leu Glu Glu
            20                  25                  30

Asn Ile Lys Lys Gly Lys Lys Cys Ile Arg Thr Pro Lys Ile Ala Lys
        35                  40                  45

Pro Val Lys Phe Glu Leu Ser Gly Cys Thr Ser Val Lys Thr Tyr Arg
    50                  55                  60

Ala Lys Phe Cys Gly Val Cys Thr Asp Gly Arg Cys Cys Thr Pro His
65                  70                  75                  80

Arg Thr Thr Thr Leu Pro Val Glu Phe Lys Cys Pro Asp Gly Glu Ile
                85                  90                  95
```

-continued

Met Lys Lys Asn Met Met Phe Ile Lys Thr Cys Ala Cys His Tyr Asn
            100                 105                 110

Cys

<210> SEQ ID NO 33
<211> LENGTH: 4049
<212> TYPE: DNA
<213> ORGANISM: Homo sapiens

<400> SEQUENCE: 33

| | | | | | |
|---|---|---|---|---|---|
| gcggccgcac | tcagcgccac | gcgtcgaaag | cgcaggcccc | gaggacccgc | cgcactgaca | 60 |
| gtatgagccg | cacagcctac | acggtgggag | ccctgcttct | cctcttgggg | accctgctgc | 120 |
| cggctgctga | agggaaaaag | aaagggtccc | aaggtgccat | cccccgcca | gacaaggccc | 180 |
| agcacaatga | ctcagagcag | actcagtcgc | cccagcagcc | tggctccagg | aaccgggggc | 240 |
| ggggccaagg | gcggggcact | gccatgcccg | ggaggaggt | gctggagtcc | agccaagagg | 300 |
| ccctgcatgt | gacggagcgc | aaatacctga | agcgagactg | gtgcaaaacc | cagccgctta | 360 |
| agcagaccat | ccacgaggaa | ggctgcaaca | gtcgcaccat | catcaaccgc | ttctgttacg | 420 |
| gccagtgcaa | ctcttctac | atccccaggc | acatccggaa | ggaggaaggt | tcctttcagt | 480 |
| cctgctcctt | ctgcaagccc | aagaaattca | ctaccatgat | ggtcacactc | aactgccctg | 540 |
| aactacagcc | acctaccaag | aagaagagag | tcacacgtgt | gaagcagtgt | cgttgcatat | 600 |
| ccatcgattt | ggattaagcc | aaatccaggt | gcacccagca | tgtcctagga | atgcagcccc | 660 |
| aggaagtccc | agacctaaaa | caaccagatt | cttacttggc | ttaaacctag | aggccagaag | 720 |
| aaccccagc | tgcctcctgg | caggagcctg | cttgtgcgta | gttcgtgtgc | atgagtgtgg | 780 |
| atgggtgcct | gtgggtgttt | ttagacacca | gagaaaacac | agtctctgct | agagagcact | 840 |
| ccctatttg | taaacatatc | tgctttaatg | gggatgtacc | agaaacccac | ctcaccccgg | 900 |
| ctcacatcta | aagggcggg | ccgtggtct | ggttctgact | ttgtgttttt | gtgccctcct | 960 |
| ggggaccaga | atctccttc | ggaatgaatg | ttcatggaag | aggctcctct | gagggcaaga | 1020 |
| gacctgtttt | agtgctgcat | tcgacatgga | aaagtccttt | taacctgtgc | ttgcatcctc | 1080 |
| ctttcctcct | cctcctcaca | atccatctct | tcttaagttg | atagtgacta | tgtcagtcta | 1140 |
| atctcttgtt | tgccaaggtt | cctaaattaa | ttcacttaac | catgatgcaa | atgttttca | 1200 |
| ttttgtgaag | accctccaga | ctctgggaga | ggctggtgtg | ggcaaggaca | agcaggatag | 1260 |
| tggagtgaga | aagggagggt | ggagggtgag | gccaaatcag | gtccagcaaa | agtcagtagg | 1320 |
| gacattgcag | aagcttgaaa | ggccaatacc | agaacacagg | ctgatgcttc | tgagaaagtc | 1380 |
| ttttcctagt | atttaacaga | acccaagtga | acagaggaga | aatgagattg | ccagaaagtg | 1440 |
| attaactttg | gccgttgcaa | tctgctcaaa | cctaacacca | aactgaaaac | ataaatactg | 1500 |
| accactccta | tgttcggacc | caagcaagtt | agctaaacca | aaccaactcc | tctgctttgt | 1560 |
| ccctcaggtg | gaaagagag | gtagtttaga | actctctgca | taggggtggg | aattaatcaa | 1620 |
| aaacckcaga | ggctgaaatt | cctaatacct | ttcctttatc | gtggttatag | tcagctcatt | 1680 |
| tccattccac | tatttcccat | aatgcttctg | agagccacta | acttgattga | taaagatcct | 1740 |
| gcctctgctg | agtgtacctg | acagtaagtc | taaagatgar | agagtttagg | gactactctg | 1800 |
| ttttagcaag | aratattktg | ggggtctttt | tgttttaact | attgtcagga | gattgggcta | 1860 |
| ragagaaagac | gacgagagta | aggaaataaa | gggrattgcc | tctggctaga | gagtaagtta | 1920 |
| ggtgttaata | cctggtagaa | atgtaaggga | tatgacctcc | ctttctttat | gtgctcactg | 1980 |

-continued

```
aggatctgag gggaccctgt taggagagca tagcatcatg atgtattagc tgttcatctg    2040
ctactggttg gatggacata actattgtaa ctattcagta tttactggta ggcactgtcc    2100
tctgattaaa cttggcctac tggcaatggc tacttaggat tgatctaagg gccaaagtgc    2160
agggtgggtg aactttattg tactttggat ttggttaacc tgttttcttc aagcctgagg    2220
ttttatatac aaactccctg aatactcttt ttgccttgta tcttctcagc ctcctagcca    2280
agtcctatgt aatatggaaa acaaacactg cagacttgag attcagttgc cgatcaaggc    2340
tctggcattc agagaaccct tgcaactcga gaagctgttt ttatttcgtt tttgttttga    2400
tccagtgctc tcccatctaa caactaaaca ggagccattt caaggcggga gatattttaa    2460
acacccaaaa tgttgggtct gattttcaaa cttttaaact cactactgat gattctcacg    2520
ctaggcgaat ttgtccaaac acatagtgtg tgtgttttgt atacactgta tgaccccacc    2580
ccaaatcttt gtattgtcca cattctccaa caataaagca cagagtggat ttaattaagc    2640
acacaaatgc taaggcagaa ttttgagggt gggagagaag aaaagggaaa gaagctgaaa    2700
atgtaaaacc acaccaggga ggaaaaatga cattcagaac cagcaaacac tgaatttctc    2760
ttgttgtttt aactctgcca caagaatgca atttcgttaa tggagatgac ttaagttggc    2820
agcagtaatc ttcttttagg agcttgtacc acagtcttgc ataagtgc agatttggct     2880
caagtaaaga gaatttcctc aacactaact tcactgggat aatcagcagc gtaactaccc    2940
taaaagcata tcactagcca agagggaaa tatctgttct tcttactgtg cctatattaa     3000
gactagtaca aatgtggtgt gtcttccaac tttcattgaa aatgccatat ctataccata    3060
ttttattcga gtcactgatg atgtaatgat atatttttc attattatag tagaatattt     3120
ttatggcaag atatttgtgg tcttgatcat acctattaaa ataatgccaa acaccaaata    3180
tgaattttat gatgtacact ttgtgcttgg cattaaaaga aaaaaacaca catcctggaa    3240
gtctgtaagt tgtttttttgt tactgtaggt cttcaaagtt aagagtgtaa gtgaaaaatc    3300
tggaggagag gataaatttcc actgtgtgga atgtgaatag ttaaatgaaa agttatggtt    3360
atttaatgta attattactt caaatccttt ggtcactgtg atttcaagca tgttttcttt    3420
ttctccttta tatgactttc tctgagttgg gcaaagaaga agctgacaca ccgtatgttg    3480
ttagagtctt ttatctggtc aggggaaaca aaatcttgac ccagctgaac atgtcttcct    3540
gagtcagtgc ctgaatcttt attttttaaa ttgaatgttc cttaaaggtt aacatttcta    3600
aagcaatatt aagaaagact ttaaatgtta ttttggaaga cttacgatgc atgtatacaa    3660
acgaatagca gataatgatg actagttcac acataaagtc cttttaagga gaaaatctaa    3720
aatgaaaagt ggataaacag aacatttata agtgatcagt taatgcctaa gagtgaaagt    3780
agttctattg acattcctca agatatttaa tatcaactgc attatgtatt atgtctgctt    3840
aaatcattta aaaacggcaa agaattatat agactatgag gtaccttgct gtgtaggagg    3900
atgaaagggg agttgatagt ctcataaaac taatttggct tcaagtttca tgaatctgta    3960
actagaattt aattttcacc ccaataatgt tctatatagc ctttgctaaa gagcaactaa    4020
taaattaaac ctattctttc aaaaaaaaa                                      4049
```

IDENTIFICATION OF GENES HAVING A ROLE IN THE PRESENTATION OF DIABETIC NEPHROPATHY

This application is the national phase under 35 U.S.C. § 371 of PCT International Application No. PCT/IE00/00026 which has an International filing date of Feb. 28, 2000, which designated the United States of America and was published in English.

TECHNICAL FIELD

This invention relates to the characterisation and identification of genes which play a role in diabetes, more particularly in the onset and progression of diabetic nephropathy and to the use of genes so characterised and/or identified as diagnostic markers for diabetic nephropathy and as the basis of drug development programmes.

BACKGROUND ART

Between 2–5% of the population develops diabetes mellitus and 20–30% of diabetics develop diabetic nephropathy. The latter accounts for over 30 % of end-stage renal failure (E.S.R.F.) requiring dialysis or transplantation in western society. The pathological hallmark of diabetic nephropathy is glomerulosclerosis due to accumulation of extracellular matrix proteins in the glomerular mesangium. Mesangial matrix accumulation reflects both increased synthesis and decreased degradation of extracellular matrix (ECM) components, and correlates with the clinical onset of proteinuria, hypertension and progressive kidney failure. Hyperglycaemia is a major stimulus for mesangial cell matrix production in diabetic nephropathy. The mechanisms by which hyperglycaemia perturb mesangial cell function are still being appreciated and include direct effects of high extracellular glucose levels and indirect effects transduced through alterations in glomerular haemodynamics and through the actions of advanced glycosylation end products.

Propagation of mesangial cells under conditions of high ambient glucose has proved a useful in vitro model with which to probe the molecular basis for mesangial matrix accumulation in diabetes, attributable to hyperglycaemia. Specifically, exposure of cultured mesangial cells to high glucose stimulates de novo synthesis of ECM components, such as type IV collagen, fibronectin and laminin, and other products that are accumulated in vivo (Ayo, S. H., et al. (1990) Am.J. Pathol. 136, 1339–1348; Wahab, N. A., et al. (1996) Biochem. J. 316, 985–992; and Ayo, S. H., et al. (1991) Am. J. Physiol. 260, F185–F191).

In view of the high morbidity and mortality rate from diabetic nephropathy in diabetics there is a need to identify stimuli which affect the onset and progression of diabetic nephropathy with the aim of preventing such onset or inhibiting or limiting the progression thereof.

DISCLOSURE OF INVENTION

The invention provides a method for identifying a gene having a role in the presentation of diabetic nephropathy, which method comprises culturing mesangial cells in a medium in the presence of a concentration of glucose sufficient to induce differential expression of a gene susceptible to such differential expression and identifying the gene so induced by suppression subtractive hybridization.

Preferably, the mesangial cells are cultured in the presence of a concentration of glucose sufficient to induce up-regulation of a gene susceptible to such up-regulation.

Further, preferably, the concentration of glucose is greater than 5 mM.

A concentration of 5 nM falls within the normal range of plasma glucose levels in a healthy human subject (4.2–6.4 mmol/l).

The concentration of glucose used is suitably in the range 5–30 mM. The concentration of 30 mM was chosen as the classic "in vitro" model of diabetic nephropathy which induces changes in mesangial function that mimic human disease. This level is also encountered in many diabetics In vivo.

In one embodiment, the mesangial cells are subjected to mechanical strain.

In a further embodiment, transforming growth factor β1 (TGF-β1) is added to the culture medium.

Suppression subtractive hybridisation (SSH) is a method based on suppressive PCR that allows creation of subtracted cDNA libraries for the identification of genes differentially expressed in response to an experimental stimulus (Gurskaya, N. G., et al. (1996) Anal. Biochem. 240, 90–97). SSH differs from earlier subtractive methods by including a normalisation step that equalises for relative abundance of cDNAs within a target population. This modification should enhance the probability of identifying increased expression of low abundance transcripts, and represents a potential advantage over other methods for identifying differentially regulated genes such as differential display-PCR (DD-PCR) (Liang, P., and Pardee, A. B. (1992) Science 257, 967–97) and cDNA-representation difference analysis (Hubank, M., and Schatz, D. G., (1994) Nucleic Acid Res. 22, 5640–5648).

To date we have used SSH to identify 150 genes differentially induced when human mesangial cells were exposed to high extracellular glucose (defined herein as 30 mM versus 5 mM) in vitro. These genes included:

(a) known regulators of mesangial cell activation in diabetic nephropathy, namely fibronectin, caldesmon, thrombospondin and plasminogen activator inhibitor-1;

(b) novel genes; and (c) genes whose induction by high glucose has not previously been reported as hereinafter described.

Prominent among the latter were genes encoding cytoskeleton-associated proteins and connective tissue growth factor (CTGF), a modulator of fibroblast matrix production. We have also demonstrated elevated CTGF mRNA levels in glomeruli of rats with streptozotocin-induced diabetic nephropathy.

In one aspect of the invention, the possibility of differential expression due to hyperosmolarity is excluded.

Hyperosmolarity is, however, a component of diabetic nephropathy and thus hyperosmolarity may represent a mechanism through which high glucose induces differential expression of certain genes having a role in the presentation of the disease.

For example, we have shown that mannitol provoked less mesangial cell CTGF expression in vitro than high glucose, excluding hyperosmolarity as the key stimulus.

High glucose also stimulated expression of transforming growth factor β1 (TGF-β1) and addition of TGF-β1 to mesangial cells triggered CTGF expression. Anti-TGF-β1 antibody blunted CTGF expression induced by high glucose. Together, these data suggest that (1) high glucose stimulates mesangial CTGF expression by TGFβ1-dependent and independent pathways, and (2) CTGF may be a mediator of TGF-β1-driven matrix production within a diabetic milieu.

CTGF may therefore be an attractive target for design of novel anti-sclerotic therapies for diabetic glomerulosclerosis.

CTGF derived from mesangial cells is a potential stimulus for increased synthesis of ECM proteins and mesangial expansion in diabetic nephropathy. The mechanisms by which high glucose triggers mesangial cell CTGF and, indeed, TGF-β, mRNA expression remain to be defined. Possible upstream triggers of CTGF transcription in response to high glucose include de novo synthesis of diacylglcerol (DAG) and subsequent activation of protein kinase C (PKC) (DeRubertis, F. R., and Craven, P., (1994) Diabetes 43, 1–8 and Fumo P., et al (1994) *Am. J. Physiol.* 267, F632–F638), non-enzymatic glycation end-products (Brownlee; M., et al. (1984) *Ann. Intern. Med* 101, 527–537 and Cohen, M. P., and Ziyadeh, F. N. (1994) *Kidney Int.* 45, 475–484) increased activity of the polyol pathway and disordered myoinositol metabolism (Goldfarb, S., et al. (1991) *Diabetes* 40, 465–471 1991) or through the recruitment of locally generated growth factors such as TGF-β1 and other mediators. (Sharma K., and Ziyadeh, F. N., (I 995) *Diabetes* 44, 1139–1146).

TGF-β1 has been implicated as the key mediator of extracellular matrix accumulation in diabetic nephropathy and other chronic renal disease . Several studies have reported increased expression of TGF-β1 in renal glomeruli in human and experimental models of diabetes (Park, I., et al. (1997) *Diabetes* 46, 473–480; Sharma, K., (1996) *Diabetes* 45, 522–530). Short term administration of TGF-β1 neutralising antibodies attenuates overexpression of mRNAs encoding matrix components and glomerulosclerosis in the STZ mouse model of diabetes (Park, I., et al. (1997) *Diabetes* 46, 473–480). CTGF shares some of the biological actions of TGF-β1such as stimulation of cell proliferation and extracellular matrix protein synthesis in fibroblasts. When considered in this context, the results described herein suggest that TGF-β1 may promote mesangial matrix production, in part, by inducing CTGF synthesis. TGF-β1 has a complex profile of biological activities that includes pro-inflammatory, pro-fibrotic and anti-inflammatory effects. By targeting CTGF it may be possible to attenuate the sclerosis-inducing effects of TGF-β1 while preserving its more desirable anti-inflammatory activities.

Novel genes identified by the method according to the invention are identified herein as IHG (Increased in High Glucose) and DHG (Down in High Glucose) and are represented by genes which include the following sequences 1, 3 and 4:

```
1)  TTGGAATAGTTCTTGCTTTATAAAAATAGTACTGCGATTAAA          (SEQ ID NO: 1)

AAAAAAGCACTTCTGCCAAAGGAACCATGTTCCAACACCGCA

AACAAGGTGTTCTGCTTAAACAGAGTAAGATACACCACCCCC

ATCCATCCCTTCCTTCCCTGTTCCCCTCCCAACTTGAGTTGTGT

CATTCGCACCAGTGTCCTGGGTGGTAGGGATGCTACAGCCAC

CTAAGGCAAGGAGCCCTGGGAGGTGGGAGGGCTTGCATGGTT

AAGCACACCAGAACTGAAGCGCAAAAGGGTCAGCTGTCTTCA

TCTAGAATCTCTGGATGTTCCTTCCAGAAAGCATCCCCGATGA

TATCGCAGTGCAAGGGCACTGGCTTTGTCCTGGTCCGGGTCAC

TGCCATCTTTTTTCCTTCCATTTCTGTTGGCAGCTTAATTTCTTT

TGTCATCACTTCATCCACCTTCTGCCATATCAACACAGTCCCTT

TCCTATACATCGGCAGCTCATTATTATAGTTGATGTTGAATTC

AGAAAACAAAATCTCATTCTTGTCTGCTGNAAGAGTTCCCTGT

AATCTCCCTTGGGCTTGTACTGGTGTTAGTCCAGATTGTTG

...........................................          (SEQ ID NO: 2)

....................................GGTCCTTTAA

AGTCTGGTTGCTGGGATACACCACGACTCTTCCGGTCAAAGCC

TGGGGGATACAGAAGGGGCTRGTCCTCAAAGTAATCCCGCCA

ATAAAACAYATAGCTGGAGGCAAACTGGGAGGYCACGTGAGT

CATGAACTTTACTGGCTCTTCTTTTAAACCAATTGGTTTTCCGC

TTGWACACAAAGCTGTACTCATCACTCTGTCCATAACGCGAT

CACAATATCCTCTAGTTCTTCCATCACAGTCTGCGCACATTTG

GTCATCAGCTGGAGAGCACGGCTGTCATTGGGTTTTGCAAAGT

TGTGCTTCTCAGCAAACCGATGGAAATTCCGGCCGTCCAGCCG

NACTACCACCCAGCAGTGTGCCAGGCAGGTGTCGTCAGCCTC
```

```
GAAGTCCCTCACGTACTCGAACTTGCTTTTTGCCATGGTCGCC

CCCAATCTCAGGTACCGTCTCAGAGTGATGGAAATGGTGGCC

AAGGAATCGTGAACCTTAACTTTACAGGCGCCCCACATTCTAC

ACGCGGAAAGGAAAGGGCCAGATAGCCCCGCCCCGGAAGTG

TTCTCTTCGTGGCTACTCTAGCCGTAGGGCGGTCATAGTCTCT

CTCGSCTCTCCCTGKAGTTCTTAAMCYYCCAGGGAAARAGGA

TGGAGGTTTAGGTTCCTCCGTTAGCACCTTCCACGCTTGCTTCT

TCCTCCTCCCGGTCTGCGGCAAATCAGTCTCACGAGGTTTTTA

AAAATTATTTTTTATCTGCTGGCCTT
```

```
              ........................ATGACACAAATATTAG        (SEQ ID NO: 3)

GATTTTATTTTTACTATTATCCACCAGCAACAAGATATCAAAC

ACTGGTTCTGTGATTATTTAATGGTGAAAAAGTTGAATAAATC

AATTTAGTATACCCATATGTTGGAATATTGAGTCCATTTTTCTT

TTAAAAATCACACTTTGGAATAATTGATGATACTGGCAAATGC

TCAAGCTGAGTGGAAAAATATATAAACATTGTATAGGCGAAT

AATTCCAATCTTGTGCATTCCCTGTGTAAACCTACATACACAA

AAAGAAAAAAGACTGAAAGGAACCATCCACAATGCTTTGATC

GGGAAAGACGGAGAAACAAAGTGTTAATTTTCTTAACTATAG

TTTTNGGTGTATTCCAGATTTTCTACAAGTTAATA  (IHG-1)

2)  GTACTTTGGATTTGGTTAACCTGTTTTCTTCAAGCCTGAGGT        (SEQ ID NO: 4)

TTTATATACAAACTCCCTGAATACTCTTTTTGCCTTGTATCTTC

TCAGCCTCCTAGCCAAGTCCTATGTAATATGGAAAACAAACA

CTGCAGACTTGAGATTCAGTTGCCGATCAAGGCTCTGGCATTC

AGAGAACCCTTGCAACTCGAGAAGCTGTTTTTATTTCGTTTTT

GTTTTGATCCAGTGCTCTCCCATCTAACAACTAAACAGGAGCC

ATTTCAAGGCGGGAGATATTTTAAACACCCAAAATGGTTGGG

TCTGATTTTCAAACTTTTAAAACTTCACTACTGATGATTCTGCA

CGCTAAGGCGAATTTGGTCCAAACACATAAGTGTGTGTTTT

GTATACACTGTATGACCCCACCCCAAATCTTTGTATTGTCCAC

ATTCTCC  IHG-2;

3)  AGAAGCAATTTAGGAANCCNACAGNAAANAAATGCTGTTTT        (SEQ ID NO: 5)

ATAGGAGAGAAAACACGGCACACCAAGGTTAAGTAGTTTGTA

GACGATGTTGAATAGGTTCAGGTACAGGTCAATGCAGTGATG

AGGAAAGCACCTANGTATACTTGACAGATAGTCCCCTTTGCTT

AACACCCAACTCCTCCACCCTGTGCAGTTTNNCTTGTGCCAGT

GATCACAGGATTCGCTGAGTGAATTACCATAATTGGATTTAAT

TCACGAAGGGGATGTTTTC  (IHG-3); and

4)  ATTGATAGAGGCCCTGTTTCATGACATTTCATGAGTTTCAAT       (SEQ ID NO: 6)

ATGTTGTTCAGCATGTTGTGAGGTGACTCTCAGCCCCTTTCCC

ACTGAGATGGACTGTGGTGATGCTGTGAGGGTGTGACTGACA
```

-continued

```
CACCTTCATGTGCCCAAGCATGGGTTTGATCACAGGTCACATG

CAGTTTTTGGCATAGTAAATGTATCATTGTTCTTTTCCTCCCTC

CTAAAGGAAACAGAGGAATCCACCTGTATGAGAGTGCCATGT

AGGGATAAACTTAAAGGACAGATGACACATTGGTCATGTTCG

TGATAAGGAAA (DHG-1).
```

The invention also provides SEQ ID NOS: 1–3, 5 and 6 set out above.

In initial studies the gene IHG-2 was assumed to be new. However, as hereinafter demonstrated IHG-2 was identified as being a formerly unknown part of the gremlin gene. We have found that mesangial cell gremlin mRNA levels are induced by high glucose, cyclic mechanical strain and TGF-β1 in vitro, and gremlin mRNA levels are elevated in the renal cortex of rats with streptozotocin-induced diabetic nephropathy in viVo. Gremlin expression was observed in parallel with induction of bone morphogenetic protein-2 (BMP-2), a target for gremlin in models of cell differentiation.

Gremlin, together with DAN and cerberus, are members of the cysteine knot super-family of proteins that have recently been shown to play important roles in limb development and neural crest cell differentiation (Hsu, D. R., et al. (1998) *Mol. Cell.* 1, 673–83; Zuniga, A., et al. (1999) *Nature* 401, 598–602). Of potential interest in the context of diabetic nephropathy, gremlin is a putative inhibitor of BMP-2 in models of neural crest cell differentiation. BMP-2 has recently been reported to have antiproliferative effects on mesangial cells.

The following Examples show that (a) IHG-2 is part of gremlin, (b) gremlin is expressed in diabetic nephropathy in vivo, (c) both glycemic and mechanical strain stimulate mesangial cell gremlin expression in vitro, (d) high glucose induces gremlin, in part, through TGFβ-mediated pathways, and (e) gremlin is a potential endogenous antagonist of BMPs within a diabetic glomerular milieu.

The invention also provides use of a gene identified by the method according to the invention:

1) as a diagnostic marker for the progression and presentation of diabetic nephropathy;

2) as an index of disease activity and the rate of progression of diabetic nephropathy; and 3) as a basis for identifying drugs for use in the prevention and/or therapy of diabetic nephropathy.

Thus, it will be appreciated that early diagnosis of diabetic nephropathy based on diagnostic markers identified in accordance with the invention can be used in conjunction with aggressive therapies to prevent full blown development of diabetic nephropathy.

The level of expression of genes identified in accordance with the invention could correlate with the degree of disease progression.

Furthermore, genes identified in accordance with the invention can represent novel therapeutic targets for drug development programmes. Once it has been established that a given gene has a designated role in the pathophysiology of diabetic nephropathy, the development of new therapeutic agents (such as, for example, small molecules, recombinant inhibitors and receptor antagonists) could be designed to inhibit expression of these genes and, thereby, prevent the development of diabetic nephropathy.

Genes identified in accordance with the invention can also be used as a clinical index of progressive renal sclerosis and scarring, as a guide to the response of progressive diabetic nephropathy to therapy and also as markers of the prevention or development thereof.

It is possible to generate mouse knock-out (k/o) models for genes identified in accordance with the invention and to generate diabetic k/o mouse models, (for example by treatment with streptozotocin) and determine if onset of diabetic nephropathy is inhibited, reduced or delayed. Thus one can determine if a given knock-out gene has a definite role in the progression and development of diabetic nephropathy.

BRIEF DESCRIPTION OF DRAWINGS

FIG. 4 is a nucleotide sequence alignment of the rat CTGF transcript and the mouse CTGF homologue fisp 12 as described in Example 3;

FIG. 5 is an amino acid sequence alignment of the rat CTGF transcript and the mouse CTGF homologue fisp 12 as described in Example 3;

FIG. 15 is the sequence of mesangial cell gremlin cDNA;

FIG. 20 is an autoradiograph of gremlin mRNA levels in the kidney cortex of a STZ-diabetic rat and an age matched control analysed by Northern Blot as described in Example 7;

FIG. 24 shows a gels depicting the outcome of RTPR analysis from the experiments of Example 9, measuring the levels of BMP-2, BMP-4 and GAPDH (control) mRNA in mesangial cells cultured for 7 days in he presence of 5 mM in or 30 mM gluose. Selective expression of BMP-2 in 30 mM glucose is detected.

Figure 1:
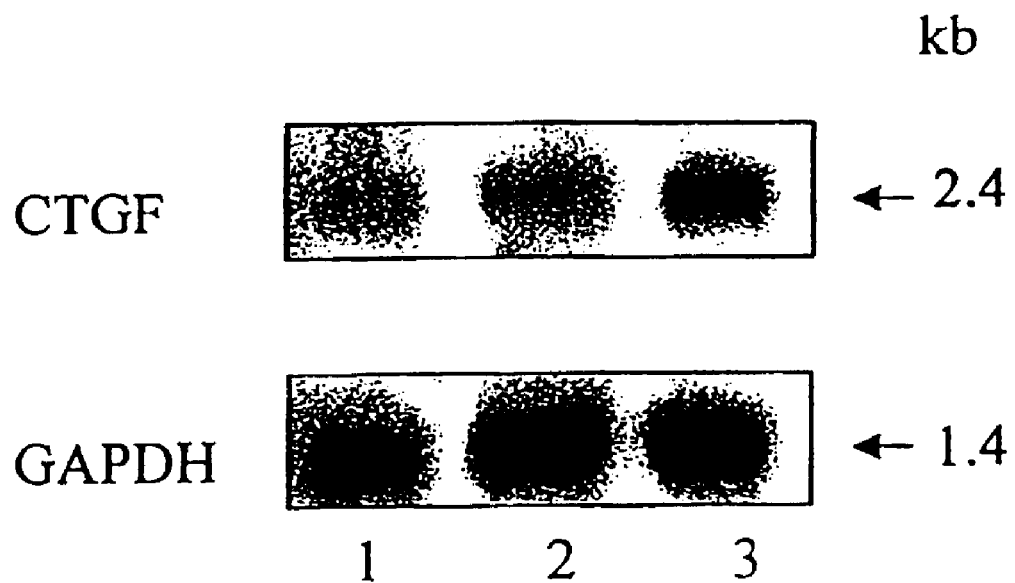
FIG. 1 is an autoradiograph of CTGF levels analysed by Northern Blot as described in Example 2.

The invention will be further illustrated by the following Examples:

MODES FOR CARRYING OUT THE INVENTION

EXAMPLE 1

Identification of Mesangial Cell Genes Differentially Induced By High Glucose a) Cell culture and streptozotocin-induced diabetic rats Primary human mesangial cells were cultured as previously reported (Brady, H. R., et al. (1992) *Kidney Int.* 42, 480–487 and Denton, M. D., et al. (1991) *Am. J. Physiol.* 261, F1071–F1079). Cells (passage 7–11) were maintained in medium (Clonetics) containing either 5 mM or 30 mM D-glucose for 7 days. Culture medium was replenished three times during this period to maintain glucose levels in the desired range. To control for the effects of hyperosmolarity, mesangial cells were cultured in media containing 5 mM glucose supplemented with 25 mM mannitol.

Male Munich-Wistar rats (260–290 g, Simonsen Laboratories) were rendered diabetic by treatment with streptozotocin (STZ; Sigma), 50 g/kg, intravenously as described previously (Zatz, R., et al. (1985). *Proc. Natl. Acad. Sci.* USA. 82, 5963–5967). At months 2 and 4 after induction of diabetic nephropathy (DN), rats were anaesthetized with intraperitoneal injection of pentobarbital (50 mg/kg), and the right kidney was excised and weighed immediately. Glomeruli were isolated from renal cortex by the standard sieving method (Brady, H. R. et al. (1992) and Denton, M. D. et al. (1991) supra). Glomerular isolation was completed within 20 minutes of removing the kidney. RNA extraction proceeded immediately thereafter.

b) RNA isolation

Polyadenlyated RNA was isolated from mesangial cells using the Microfast Track (Microfast Track is a Trade Mark) kit (Invitrogen). Total RNA was isolated from glomeruli using RNAzol solution (TEL-test Inc.).

c) Suppression subtractive hybridisation (SSH)

SSH was performed with the PCR-SELECT cDNA subtraction kit (Clontech) as directed by the manufacturer with the modification that a four-fold greater than recommended amount of driver cDNA was added to the second hybridisation. Starting material consisted of 2 μg of mesangial cell mRNA cultured in 30 mM D-glucose for 7 days as "tester" and 2 μg of mesangial cell mRNA cultured in 5 mM D-glucose for 7 days as "driver". Thirty primary PCR cycles and 12 secondary PCR cycles were performed.

d) Cloning and sequencing of cDNAs

PCR products generated by SSH were subcloned into the PCR 2.1 vector using the original TA cloning kit (Invitrogen). Subcloned cDNAs were isolated by colony PCR amplification. Sequencing was performed using an automated ABI 370A DNA sequencing system. Sequence reactions were carried out with the ABI prism dye terminator cycle sequencing ready reaction kit (Perkin Elmer). The sequences obtained were compared against GenBank/EMBL and Expressed Sequence Tag (EST) databases using BLAST searches.

SSH analysis suggested differential induction of 16 mRNAs in primary cultures of human mesangial cells propagated for 7 days in 30 mM glucose. Northern Blots performed using formaldehyde denaturation according to standard protocols and quantitated using a Phosphor Imager (Biorad) confirmed differential expression of fifteen of the sixteen subcloned fragments as indicated in Table 1.

In Table 1[a] refers to the sequence identity based on comparisons with the Genbank/EMBL database;

[b] refers to an estimate of the size (kb) of the mRNA identified by Northern Blot analysis; and

[c] refers to the differential expression of each gene based on Northern Blot analysis of primary human mesangial cells cultured under indicated conditions relative to expression in cells cultured in 5 mM glucose. Values were obtained by Phosphor-Imaging and were normalised by comparison with glyceraldehyde-3-phosphate dehydrogenase (GAPDH) (*, detected in mesangial cells cultured in 5 mM glucose+25 mM mannitol and 30 mM glucose, but not in 5 mM glucose, fold expression is degree of expression relative to that found in 5 mM glucose).

TABLE 1

Summary of cDNAs identified by SSH as being induced in mesangial cells cultured in high glucose.

| | | Differential Expression[c] | |
|---|---|---|---|
| Gene[a] | mRNAbk[b] | 30 mM glucose | 25 mM mannitol + 5 mM glucose |
| Extracellular Matrix Proteins | | | |
| Fibronectin | 7.0 | 2.1-fold | 1.5-fold |
| Thrombospondin | 6.0 | 7.0-fold | 8.0-fold |
| Actin-Binding Proteins | | | |
| MRLC | 0.9 | 3.9-fold | 1.6-fold |

TABLE 1-continued

Summary of cDNAs identified by SSH as being induced in mesangial cells cultured in high glucose.

| | | Differential Expression[c] | |
|---|---|---|---|
| Gene[a] | mRNAbk[b] | 30 mM glucose | 25 mM mannitol + 5 mM glucose |
| T-plastin | 1.2 | 4.2-fold | 1.8-fold |
| Caldesmon | 3.6 | 3.3-fold | 2.8-fold |
| Profilin | 1.0 | 2.2-fold | 2.3-fold |
| CAP | 2.6 | 1.5-fold | 1.7-fold |
| ARP3 | 2.5 | 2.0-fold | 1.0-fold |
| Growih Factors | | | |
| CTGF | 2.4 | 3.0-fold | 1.5-fold |
| Others | | | |
| PAI-1 | 2.0 | 1.2-fold | 1.0-fold |
| | 3.0 | 3.9-fold | 2.0-fold |
| RBM3 | 1.5 | 1.8-fold | 1.4-fold |
| Ubiquitin | 3.0 | 2.3-fold | 1.7-fold |
| TCTP | 0.8 | 4.3-fold | 2.5-fold |
| IHG-1 | 3.4 | * | * |
| IHG-2 | 2.5 | 2.0-fold | 2.0-fold |

Sequence analysis revealed induction of four genes implicated previously in the pathogenesis of diabetic nephropathy: fibronectin, caldesmon, PAI-1, and thrombospondin. Of eleven other cDNA fragments, one encoded a novel gene, designated herein as IHG-1and ten encoded known genes, including IHG-2 as hereinafter described, whose induction by high glucose had not been reported previously. Prominent among the latter genes were connective tissue growth factor (CTGF) and several cytoskeleton-associated proteins, namely profilin, caldesmon, adenyl cyclase-associated protein (CAP), actin-related protein-3 (ARP3), T-plastin, and myosin regulatory light chain (MRLC). Subsequent studies focused on induction of CTGF, a regulator of matrix production in several model systems as described in Examples 2 and 3. The prominence of genes encoding multiple actin-binding proteins is also noteworthy, given recent reports implicating F-actin disassembly in the pathogenesis of mesangial cell dysfunction and glomerular hypertension in diabetic nephropathy (Zhou, X., et al. (1995) *Lab. Invest.* 73, 372–383 and Zhou, X. Lai, et al. (1997) *Kidney Int.* 51, 1797–1808). The induction of profilin expression is particularly interesting given its role as a regulator of actin polymerization under conditions of cell stress (Sohn, R. H. and Goldschmidt-Clermont, P. J. (1994) *Bioessays* 16, 465–472).

Within a diabetic milieu, high glucose levels may perturb cellular function through glucose-specific actions or by increasing the osmolarity of extracellular fluids. The role of hyperosmolarity as a mediator of gene induction by high glucose was assessed by comparing mRNA levels, as determined by Northern Blot, in cells cultured in either 30 mM glucose or in 5 mM glucose supplemented with 25 mM mannitol. High glucose was more effective than high osmolarity at inducing expression of CTGF, myosin regulatory light chain (MRLC), actin related protein 3 (ARP3), T-plastin and translationally controlled tumor protein (TCTP). High glucose and mannitol-induced hyperosmolarity afforded equivalent induction of the other products.

EXAMPLE 2

CTGF Expression in Mesangial Cells Cultured in High Glucose a) Influence of high ambient glucose on CTGF mRNA levels in human mesangial cells.

CTGF, is a 38 kD cysteine-rich secreted peptide known to modulate ECM production in some extrarenal cell types. In Example 1, SSH analysis identified a cDNA fragment of 250 bp which was identical to bases 814–1061 of the human CTGF cDNA. Induction of CTGF mRNA expression in primary human mesangial cells cultured in high glucose was investigated by Northern Blotting as shown in FIG. 1.

In FIG. 1 the lanes represent the following:

Lane 1: RNA from mesangial cells exposed to 5 mM glucose;

Lane 2: RNA from mesangial cells exposed to 5 mM glucose and 25 mM mannitol;

Lane 3: RNA from mesangial cells exposed to 30 mM glucose for seven days.

Figure 2:
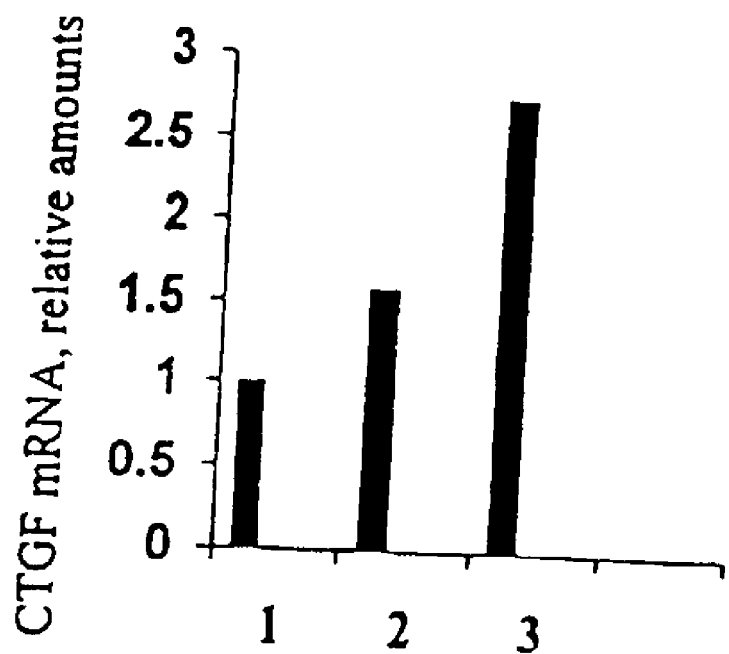
FIG. 2 is a graph of the relative amount of CTGF MRNA as estimated by Phosphor Imager quantification as described in Example 2.

A 2.4 kb band was detected following hybridisation with the CTGF probe. The relative amounts of CTGF mRNA as estimated by Phosphor Imager quantification are indicated in FIG. 2. All of the values were normalised to GAPDH levels and the results are representative of three independent experiments.

The results indicate that CTGF mRNA expression was between 2.5–3.3-fold higher in mesangial cells cultured in 30 mM glucose as compared with 5 mM glucose.

b) Effect of CTGF on mesangial cell matrix production.

To investigate the direct effects of CTGF up-regulation on matrix production, in particular the effect on collagens I and IV and fibronectin, mesangial cells were incubated with recombinant CTGF protein.

Mesangial cells were serum starved for 24 hr in RPMI 1640 medium supplemented with 0.5 % fetal bovine serum (FBS) and then exposed to rhCTGF (8 ng/ml) (a generous gift from Dr. Gary Grotendorst) for 24 hr (Kreisberg, J. I. and Ayo, S. H. (1993). *Kidney Int.* 43, 109–113). Total RNA was extracted and chromosomal DNA was removed using DNase 1 (Gibco-BRL). Equal amounts of cDNA were subsequently amplified by PCR using specific primers for GAPDH (Gen/EMBL accession no. AJ005371, sense: ACCACAGTCCATGCCATCAC (SEQ ID NO: 7); antisense: TCCACCACCCTGTTGCTGTA (SEQ ID NO: 8), Collagen I (Gen/EMBL accession no. X55525, sense: GGTCTTCCTGGCTTAAAGGG (SEQ ID NO: 9); antisense: GCTGGTCAGCCCTGTAGAAG (SEQ ID NO: 10)), Collagen IV (Gen/EMBL accession no. M11315, sense: CCAGGAGTTCCAGGATTTCA (SEQ ID NO: 11); antisense: TTTTGGTCCCAGAAGGACAC (SEQ ID NO: 12) and fibronectin (Gen/EMBL accession no. X0276 1, sense: CGAAATCACAGCCAGTAG (SEQ ID NO. 13), antisense: ATCACATCCACACGGTAG (SEQ ID NO: 14)).

Figure 3:
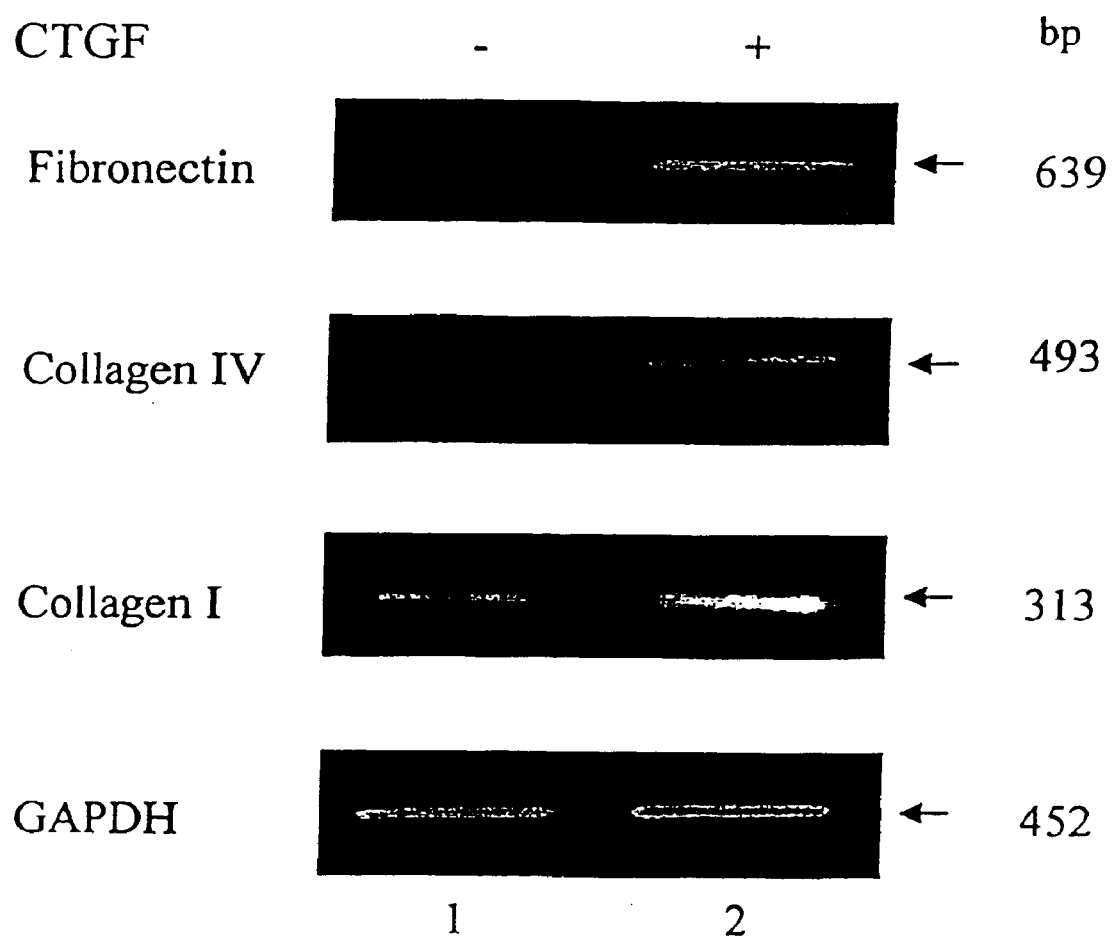
FIG. 3 is a 2% agarose gel showing ethidium-stained PCR products as described in Example 2.

FIG. 3 depicts ethidium-stained panels of a 2% (w/v) agarose gel containing 10 μl of each PCR reaction after electrophoresis.

In FIG. 3 the lanes represent the following:

Lane 1: RT-PCR products from mesangial cells cultured in RPMI 1640 and 0.5% FBS;

Lane 2: RT-PCR products from mesangial cells exposed to rhCTGF (8 ng/ml) for 24 hr.

These results indicate that rhCTGF up-regulates mesangial cell collagens I and IV and fibronectin. These proteins typify matrix accumulation as seen in diabetic nephropathy.

CTGF is a member of a small family of highly homologous proteins termed the CCN family (for CTGF / fisp-12, cef10/cyr61 and Nov) (Bork, P (1993). *FEBS Letts.* 327, 125–130.). These peptides are characterised by conservation of 38 cysteine residues that constitute more than 10 % of the amino acid content. All members have signal peptides and appear to be secreted via orthodox secretory pathways (Bradham, D. M., (1991) *J. Cell. Biol.* 114, 1285–1294). In the context of diabetic nephropathy, it is intriguing that CTGF which is up-regulated in the presence of ambient glucose, in turn, up-regulates the production of extracellular matrix (ECM). These data demonstrate the potential of CTGF as a stimulus for increased ECM synthesis and mesangial expansion in diabetic nephropathy.

EXAMPLE 3

Enhanced CTGF Expression in Renal Cortex and Isolated Glomeruli of Rats with STZ-induced Diabetic nephropathy.

To assess CTGF expression in diabetic nephropathy in vivo, CTGF mRNA levels were measured in RNA isolated from the cortex of rats with STZ-induced diabetes mellitus. To this end, PCR primers for rat CTGF were designed from the sequence of the mouse CTGF homologue, fisp12 (Genbank/EMBL accession no. M70642, sense: CTAA-GACCTGTGGAATGGGC (SEQ ID NO: 15); antisense: CTCAAAGATGTCATTGTCCCC (SEQ ID NO: 16)) (Ryseck, R. P., (1991) *Cell Growth Differ.* 2, 225–233).

RT-PCR was performed on total RNA extracted from renal cortex of STZ-diabetic rats and age matched controls. The sequence of the rat CTGF transcript was 94% identical at the nucleotide level (FIG. 4) and 99% identical at the amino acid level (FIG. 5) to the mouse CTGF homologue fisp12 (bases 783–1123, accession no. M70642). Nucleotides that differ between the two species are given in upper case and the single different amino acid is in bold.

Figure 6:
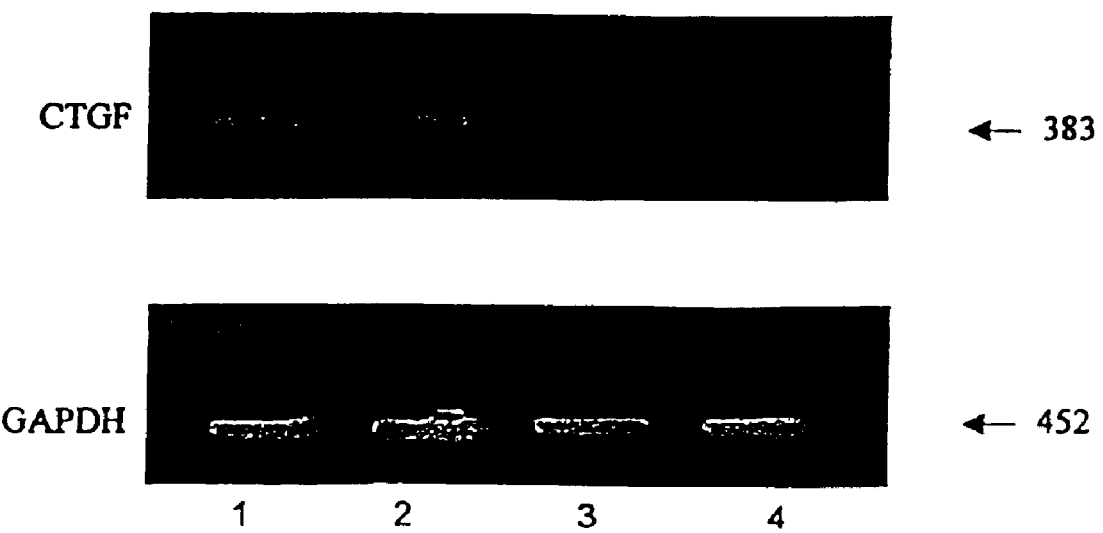
FIG. 6 is a 2% agarose gel showing ethidium-stained PCR products as described in Example 3.

Induction of CTGF mRNA was observed in the renal cortex of rats with STZ-induced diabetic nephropathy at four months after administration of STZ, coincident with mesangial expansion and proteinuria as shown in FIG. 6 and data not shown.

FIG. 6 depicts ethidium-stained panels of a 2% (w/v) agarose gel containing 10 μl of each PCR reaction after electrophoresis. CTGF and GAPDH MRNA levels were analysed in total RNA purified from 2 diabetic animals with established nephropathy after four months of diabetes (lanes 1 and 2) and two age matched control animals (lanes 3 and 4).

CTGF expression was further localized to glomeruli by RT-PCR analysis of RNA extracted from glomeruli isolated by differential sieving from the renal cortex of rats with STZ-induced diabetic nephropathy. Glomerular levels of CTGF mRNA were increased by 2.5-fold and 1.6-fold after two months and four months of diabetes, respectively, by comparison with age and sex-matched controls. The significance of these observations is further supported by a recent report demonstrating CTGF expression in a screen of human renal diseases including diabetic nephropathy (Ito, Y., et al. (1998) *Kidney Int.* 53, 853–861).

EXAMPLE 4

Induction of Mesangial Cell CTGF Expression by High Glucose Involves TGF-β1Dependent and Independent Pathways.

It has been shown that TGF-β1 is a stimulus for mesangial matrix accumulation in diabetic nephropathy. In our experimental model as described in Example 1, high glucose concentrations provoked induction of TGF-β1 mRNA expression in cultured human mesangial cells over the same temporal framework as CTGF expression (data not shown).

To assess the role of TGF-β1 as a stimulus for CTGF expression in response to high glucose, cells were incubated in either 5 mM glucose or 30 mM glucose plus 1 μl/ml anti-TGF-β1 antibody for seven days with three changes of medium. Cells were serum starved for 24 hr in RPMI 1640 and 0.5% FBS. 10 ng/ml TGF-β1 Calbiochem) or 10 ng/ml TGF-β1 preadsorbed with 1 μg/ml neutralising anti-TGF-β1 polyclonal antibody were subsequently added for 24 hr.

The role of PKC on CTGF expression in response to high glucose was investigated by culturing the mesangial cells in either 5 mM, 30 mM glucose or 30 mM glucose and the PKC inhibitor GF 102903X.

Figure 7:
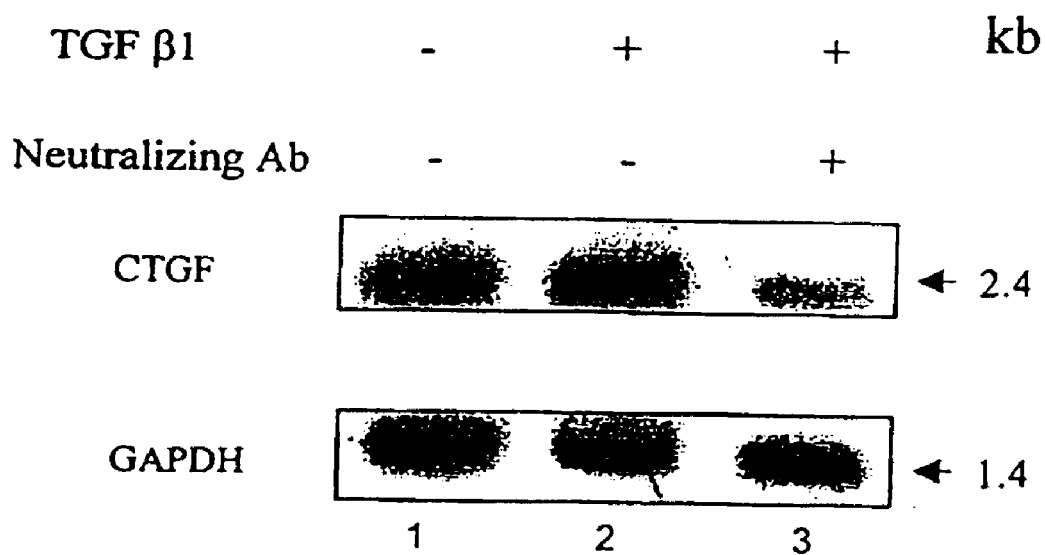
FIG. 7 is an autoradiograph of CTGF levels in the presence of TGF-β1 and TGF-β1 neutralising antibodies analysed by Northern Blot as described in Example 4.
Figure 8:
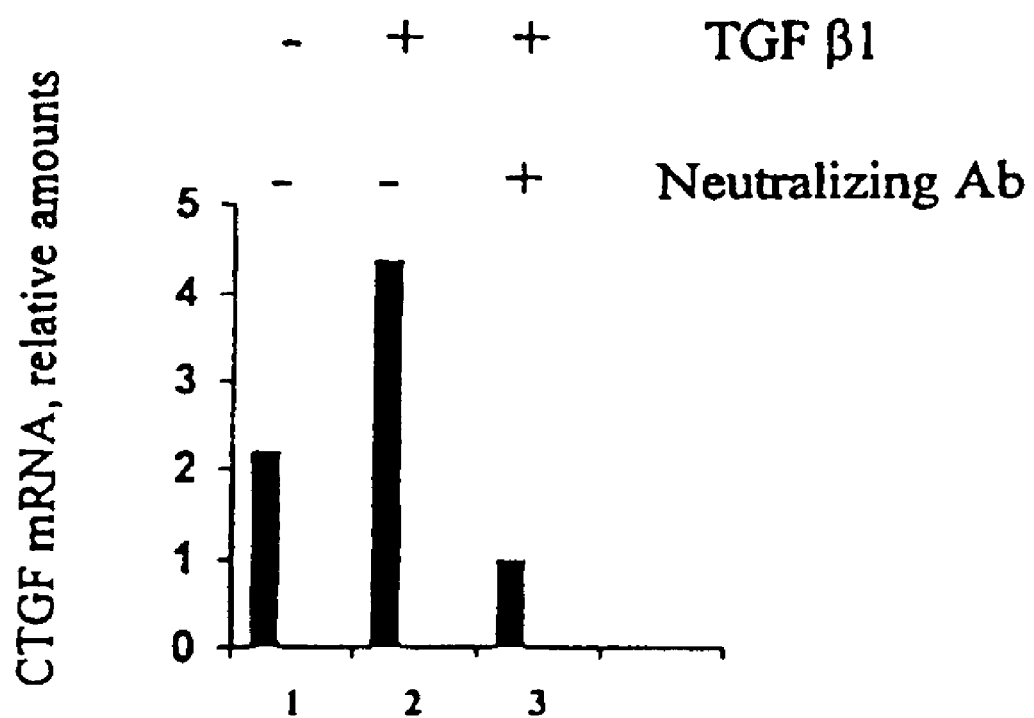
FIG. 8 is a graph of the relative amount of CTGF mRNA as estimated by Phosphor Imager quantification as described in Example 4.

FIG. 7 is an autoradiograph of CTGF mRNA levels analysed by Northern Blot and depicts the results obtained when mesangial cells were exposed to TGF-β1 (10 ng/ml) for 24 hr in the presence (lane 3) and absence (lane 2) of anti-TGF-β1 neutralising antibody (1 μg/ml). Cells cultured in RPMI 1640 and 0.5% FBS for 24 hr served as control (lane 1). A 2.4 kb band was detected following hybridisation to the CTGF probe. The blot was stripped and reprobed with GAPDH. The relative amount of CTGF mRNA as estimated by Phosphor Imager quantification (FIG. 8). Values were normalised to GAPDH levels and the results are representative of two independent experiments.

These results indicate that TGF-β1 is a potent inducer of increased CTGF mRNA levels under these conditions. This effect was inhibited by the addition of a neutralising anti-TGF-β1 antibody as depicted in FIG. 7.

Figure 9:
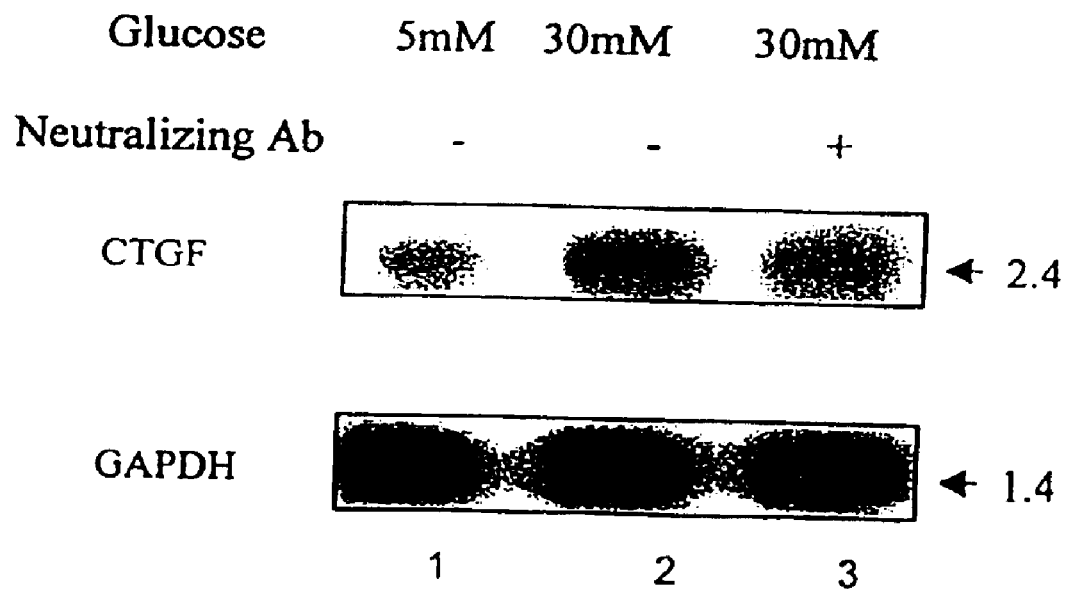
FIG. 9 is an autoradiograph of CTGF levels in the presence of varying amounts of glucose and TGF-β1 neutralising antibodies analysed by Northern Blot as described in Example 4.
Figure 10:
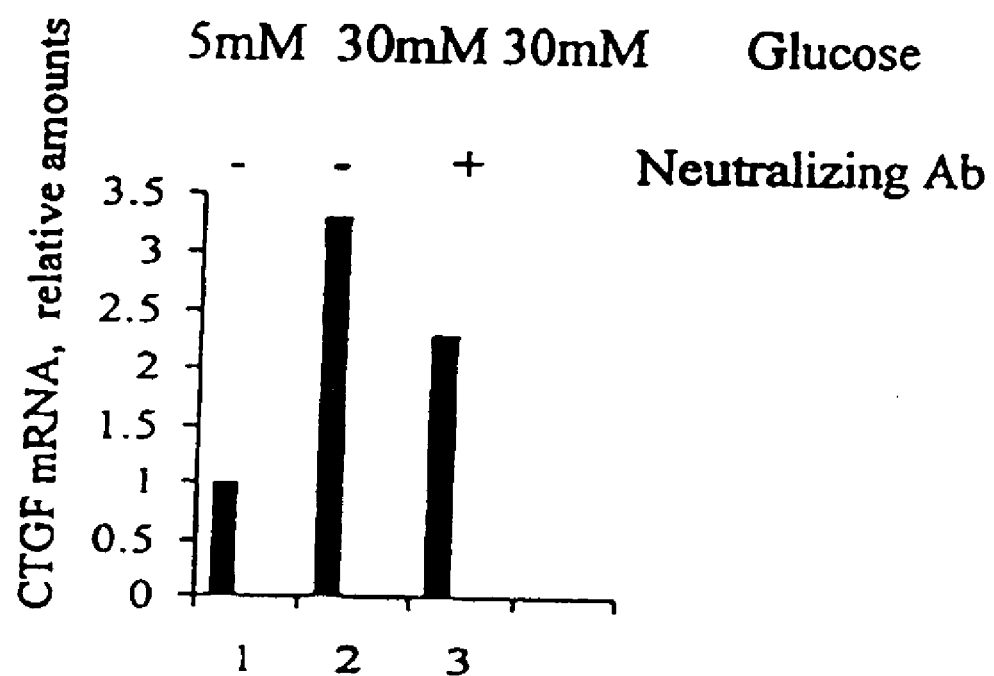
FIG. 10 is a graph of the relative amount of CTGF mRNA as estimated by Phosphor Imager quantification as described in Example 4.

FIG. 9 is an autoradiograph of CTGF mRNA levels analysed by Northern Blot and depicts the results obtained when mesangial cells were exposed to 5 mM glucose (lane 1), 30 mM glucose (lane 2) and 30 mM glucose in the presence of anti-TGF-β1 neutralising antibodies (1 μg/ml) (lane 3) for seven days. A 2.4 kb band was detected following hybridisation to the CTGF probe. The blot was stripped and probed with GAPDH. The relative amount of CTGF MRNA as estimated by Phosphor Imager quantification (FIG. 10). Values were normalised to GAPDH levels.

The neutralising anti-TGF-β1 antibody partially attenuated the glucose-induced increase in CTGF transcript level in mesangial cells grown in 30 mM glucose for 7 days (FIG. 9), suggesting that high glucose triggers mesangial cell CTGF expression through TGF-β1-dependent and independent pathways.

Figure 11:
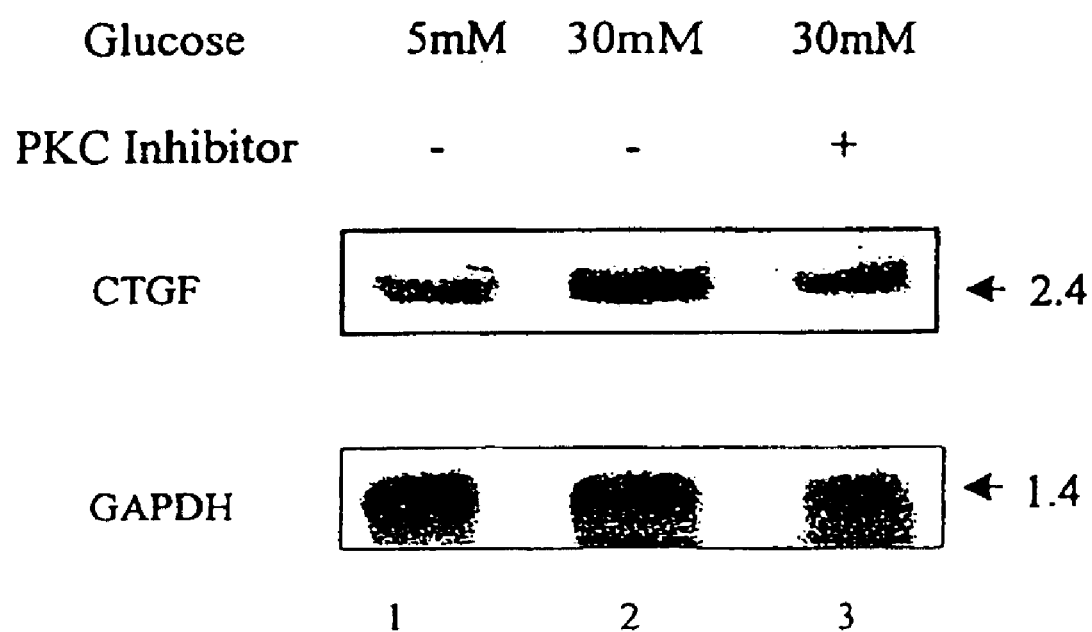
FIG. 11 is an autoradiograph of CTGF levels in the presence of varying amounts of glucose and PKC inhibitor GF102903X analysed by Northern Blot as described in Example 4.
Figure 12:
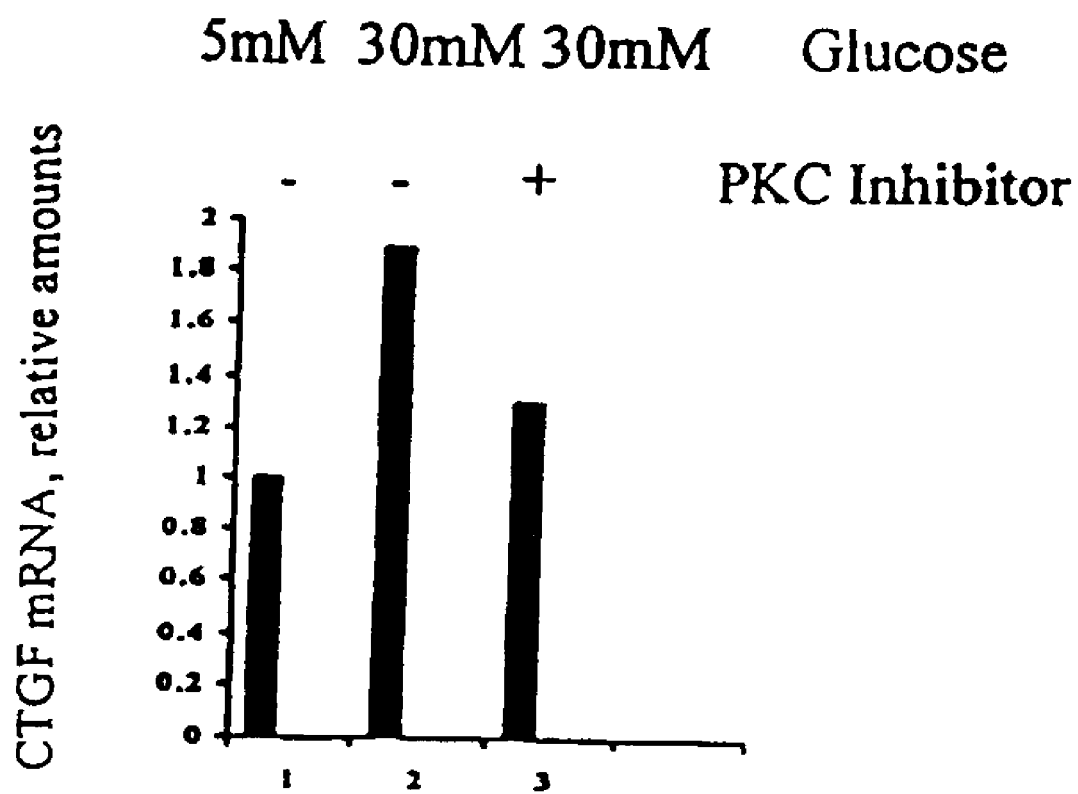
FIG. 12 is a graph of the relative amount of CTGF MRNA as estimated by Phosphor Imager quantification as described in Example 4;.

FIG. 11 is an autoradiograph of CTGF mRNA levels analysed by Northern Blot and depicts the results obtained when mesangial cells were exposed to 5 mM glucose (lane 1), 30 mM glucose (lane 2) and 30 mM glucose in PKC inhibitor GF102903X (10 μM) (lane 3) for four days. A 2.4 kb band was detected following hybridisation to the CTGF probe. The blot was stripped and probed with GAPDH. The relative amount of CTGF mRNA as estimated by Phosphor Imager quantification (FIG. 12). Values were normalised to GAPDH levels.

Whereas the PKC inhibitor GF102903X was without effect on TGF-β1-induced CTGF expression in our system (data not shown), this compound afforded partial inhibition of high glucose-induced CTGF expression (FIG. 11).

CTGF shares some of the biological actions of TGF-β1such as stimulation of cell proliferation and extracellular matrix protein synthesis in fibroblasts. When considered in this context, our results suggest that TGF-β1 may promote mesangial matrix production, in part, by inducing CTGF synthesis. TGF-β1 has a complex profile of biological activities that includes pro-inflammatory, pro-fibrotic and anti-inflammatory effects. By targeting CTGF it may be possible to attenuate the sclerosis-inducing effects of TGF-β1 while preserving its more desirable anti-inflammatory activities.

EXAMPLE 5

Further Characterisation of IHG-2

Figure 13:
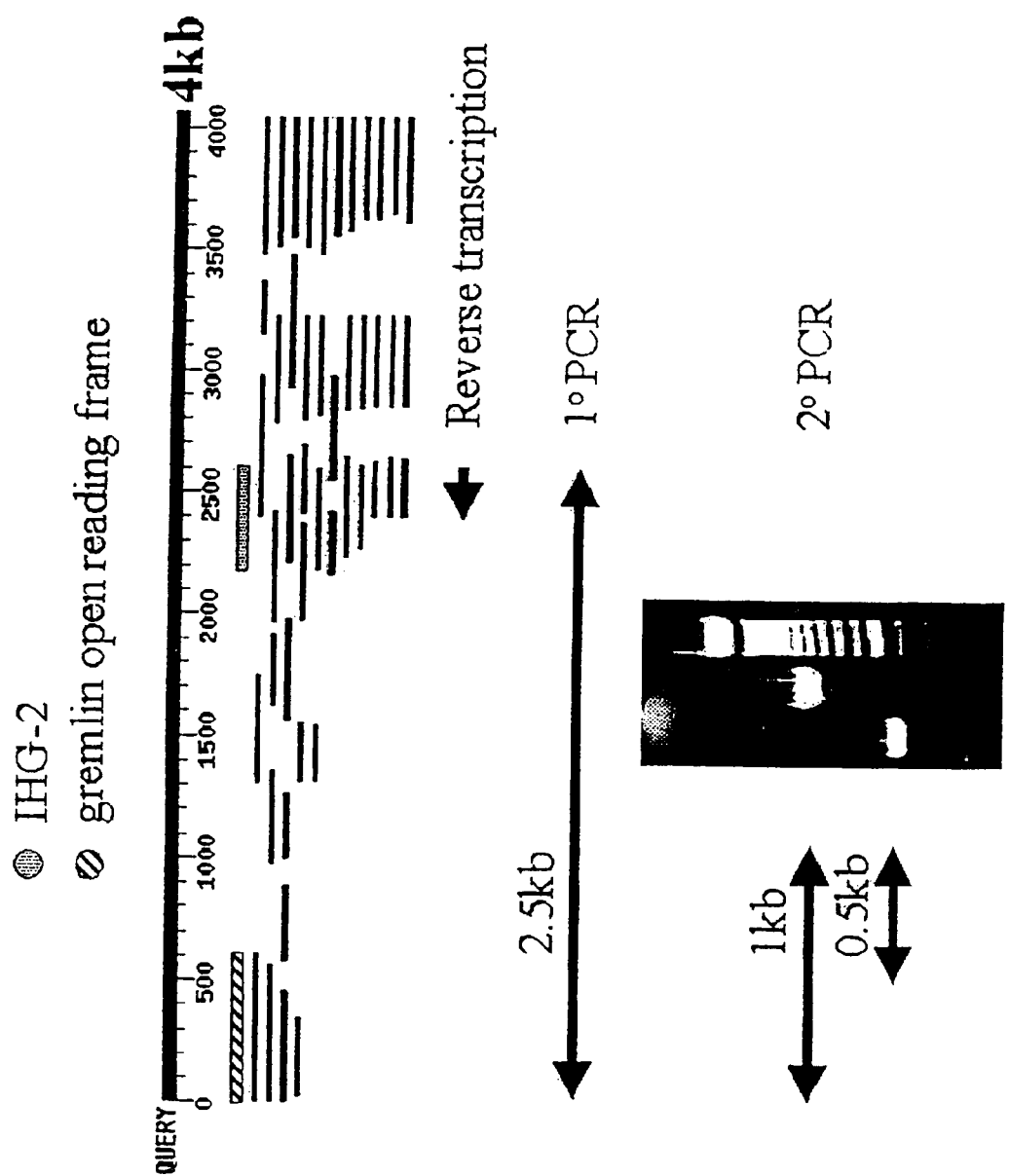
FIG. 13 is a graphical representation of a BLAST output from the EST database as described in Example 6 and a gel depicting the successful PCR amplification of fragments of the human gremlin mRNA transcript from human mesangial cells. The gel shows that unambiguous association of the fragment cloned in the SSH analysis with the human gremlin open reading frame (ORF) could be achieved by PCR using 3'-primer from the cloned sequence and a 5'-primer from the ORF sequence, in the database, to generate a primary PCR product of 2.5 kb.

IHG-2 is a mesangial cell gene which we have identified as being induced in human mesangial cells by high extracellular glucose as described in Example 1. To further characterise this gene, IHG-2 was searched against the dbEST using the BLAST algorithm. This search identified a clone that was 94% identical to ESTAA071138, clone no: 530117 3'. The sequence for the 5' end of this clone was also in the database, which again identified multiple ESTs. These ESTs showed homology with the 3' untranslated region (UTR) of a rat cDNA clone known as drm/Gremlin. As indicated above, gremlin/drm, together with DAN and cerberus, are members of the cysteine knot super-family which includes TGFβ and bone morphogenetic protein (BMP). A second EST W48852, clone no:324951 3', was identified from the IHG-2 BLAST. The 5' end of this clone, EST W48619, was also searched against the database, from which EST AA373348 was obtained. This clone showed homology with the drm 3' UTR, approximately 500 bp from the open reading frame (ORF). Thus, it was possible to make a direct link from IHG-2 to within 500 bp of the ORF of drm/gremlin. Therefore, by establishing a link between EST AA37348 and the ORF of drm/gremlin, it was confirmed that IHG-2 is part of the 3' UTR of this gene. Primers were designed to recognise the ORF, IHG-2, and the EST clone AA373348. An initial PCR using primers corresponding to the start site of the gremlin/drm gene together with a primer within the IHG-2 clone would give a predicted product of approximately 2.5 kb. This product was nested with primers corresponding to the 3' end of the ORF of gremlin and the EST clone AA373348, generating a product of approximately 500 bp, thus verifying that this EST is in the UTR of the human drm/gremlin gene. Therefore, IHG-2 was found to be part of the drm/gremlin gene, which was not previously known (FIG. 13).

EXAMPLE 6

Use of Cloning In-Silico Coupled with PCR to Demonstrate that IHG-2 is Part of the 3' Untranslated Region of Gremlin In Example 5 we describe the identification of a transcript, IHG-2, the sequence of which did not show homology against the cumulative database of characterised sequences using the BLAST algorithm.

Bioinformatic analysis was carried out as follows:

Database searching and alignments were performed at the National Center for Biotechnology Information (NCBI) Bethesda, Md., U.S.A. using the Basic Local Alignment Search Tool Algorithm (BLAST) (Altschul, S. F., et al. (1997) *Nucleic Acids Res.* 25, 3389–3402). The Non Redundant (nr) and the Expressed Sequence Tag (EST) databases were sourced. Contiguous sequences were generated using Fragment Assembly, a program within the Genetics Computer Group Inc. package. UniBlast (Guffanti, A., and Simon, G., *Trends in Genetics,* 14, 293) was used to identify homologous clusters within the UniGene database and to verify the consensus sequence derived from ESTs. Chromosomal localization data were obtained from the UniGene and Online Mendelian Inheritance in Man (OMIM) databases.

To further characterise the sequence, the sequence of IHG was searched against the EST database where a number of matches were obtained. Each of these matches was, in turn, searched against the nr database at NCBI. Four ESTs, namely W52686, N28395, H80042, and W47324, showed low homology to the 3' UT region of the rat gene drm referred to in Example 5. The ORF of the human homologue of this gene, gremlin, was also in the database.

To generate a link between the ORF of gremlin and IHG-2, successive BLAST searches were used to identify overlapping sequences in the EST database.

However, it was not possible to directly link IHG-2 to the ORF of gremlin with sequences within the EST database. Therefore, RNA isolated from human mesangial cells was reverse transcribed with a primer that recognises IHG-2. PCR analyses were performed spanning the regions shown in FIG. 13.

In this graphical representation of a BLAST output from the EST database, the thick bar of 4 kb represents the final composite sequence of the gremlin gene. Each of the other bars represents an individual sequence, in the EST database, that were assembled, where possible, into continuous sequences, and demonstrates how cloning in-silico was used to generate the contiguous sequence. The region of no EST overlap was generated by reverse transcription of human mesangial mRNA with a complementary primer to IHG-2. PCR was performed spanning the regions indicated (by arrows), and the resulting products were sequenced, allowing a contiguous cDNA of 4049 bp to be generated which included the open reading frame of gremlin and IHG-2.

Figure 14:
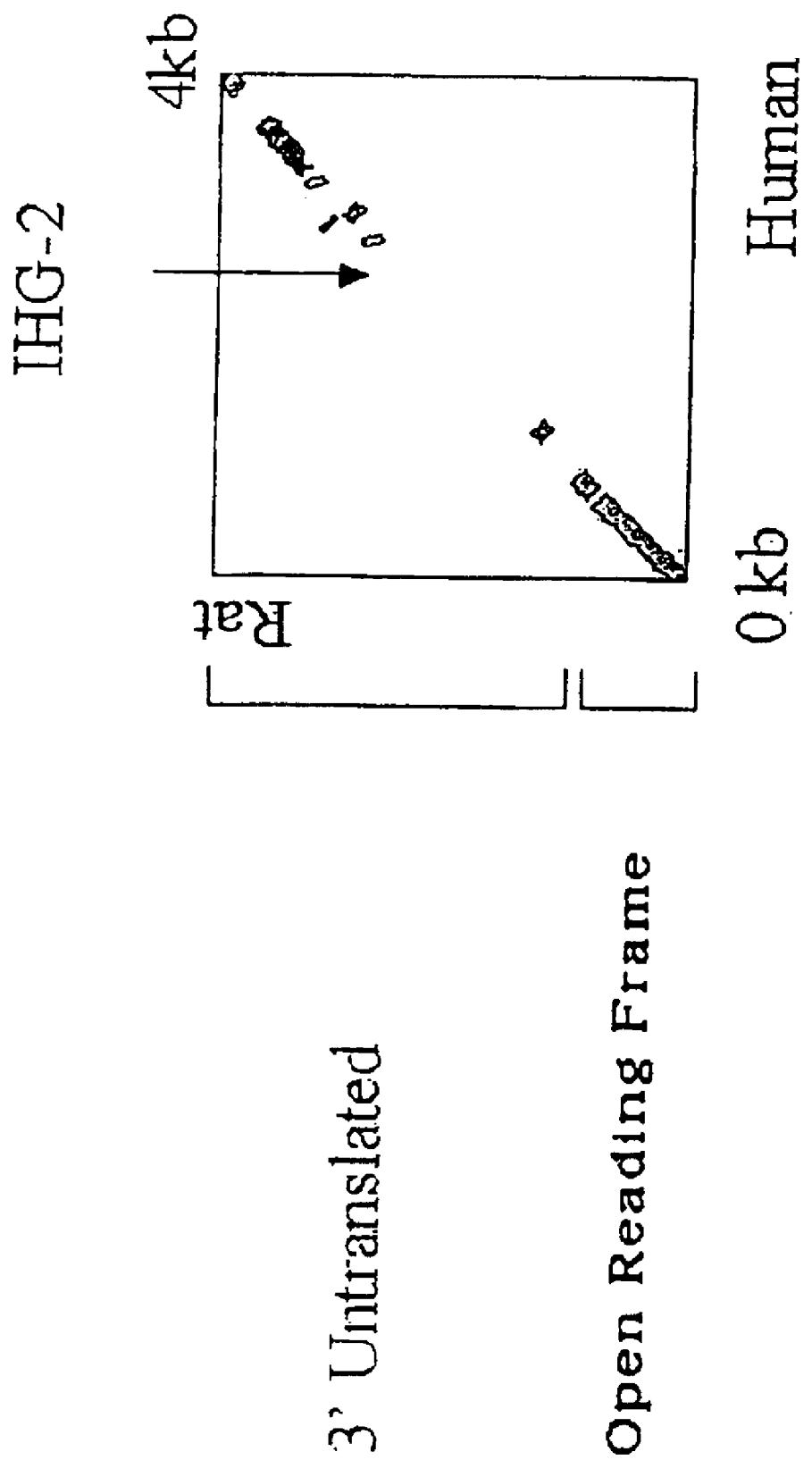
FIG. 14 is a graphical representation of the alignment of human gremlin and rat drm when compared using the BLAST algorithm as described in Example 6.

Human gremlin and rat drm cDNAs were compared and FIG. 14 shows a graphical representation of an alignment between rat drm and human gremlin together with the region corresponding to IHG-2 using the BLAST algorithm. Sequence homology was found to be high in the coding region of the cDNA; however, there are only small regions of homology within the 3' UT region. This explains why IHG-2 did not identify drm in a BLAST search, but a match to drm, and thus gremlin, was obtained by examining EST sequences further. The lack of homology between rat drm and human gremlin probably results from decreased selective pressure on the 3' UT region of gene homologues to remain the same between species.

FIG. 15 shows the final sequence of human mesangial cell gremlin, indicating the ORF and the region corresponding to IHG-2 (GenBank accession no: AF110137). Shown are the 5' and 3' UT sequence, and the open reading frame (with translation). The boxed region corresponds to the location of IHG-2. At the time of submission, this sequence matched 136 separate EST entries in the EST database. Of these entries, 23.5% were derived from fibroblast libraries; 30% were from bone tissue libraries; and 34% were derived from tumor related libraries. The sequence was also searched against the UniGene database using the UniBlast program. This identified 4 UniGene clusters, Hs.214148, Hs.40098, Hs.1 14330, and Hs.239507. Two of these clusters, Hs.40098, and Hs.239507, have been mapped to intervals D15S118–144 and D15S144–165 on chromosome 15, respectively. Secretory granule neuroendocrine protein 1 and the alpha polypeptide of the nicotinic cholinergic receptor have been mapped to either side of these clusters and have also been mapped more specifically to the 15q11–15 interval. Analysis of the OMIM database reveals that the formin gene, which was recently shown to induce gremlin expression in the developing limb bud (Zuniga, A., et al. (1999) supra ), is also localised to this interval. Diabetes mellitus with multiple epiphyseal dysplasia, or Wolcott-Rallison syndrome, is localised to the 15q11–12 interval (Stewart, F. J., et al., (1996) *Clin. Genet.* 49, 152–5). In the epiphyseal growth plate, immunohistochemical studies have revealed that BMP-2 and 4 are expressed in proliferating and maturing chrondocytes, suggesting that BMP and its receptors play roles in the multi-step cascade of enchondral ossification (Yazaki, Y., et al., (1998) *Anticancer Res.* 18, 2339–44). Regulation of gremlin expression may have implications in both of the disease states associated with Wolcott-Rallison syndrome.

EXAMPLE 7

Induction of Mesangial Cell Gremlin Expression in vitro by High Glucose and Cyclic Mechanical Strain Induce A) Primary cultures of human mesangial cells were propagated as described in Example 1, except that the medium was supplemented with 5% FBS. Treatment of cultures with glucose was carried out as described in Example 1. Mesangial cells were exposed to either 5 mM glucose or 30 mM glucose for seven days.

Northern Blot analysis as described further below was performed on RNA extracted from mesangial cells grown in either 5 mM ('normal') or 30 mM ('high') glucose using the ORF of gremlin and IHG-2 probes. Both probes detected a 2-fold increase in gene expression under high glucose conditions as depicted in FIG. 16.

All subsequent northern analysis was performed using the ORF of gremlin as a probe.

Northern Blots were performed using formaldehyde denaturation according to standard protocols and quantitated using a phosphorimager (Biorad). PCR products used to generate the probes for northern analysis were amplified using primers for the open reading frame (ORF) of gremlin (sense: ATGAGCCGCACAGCCTACAC (SEQ ID NO: 17); antisense TTAATCCAAATCGATGGATATGC (SEQ ID NO: 18)), and for IHG-2 (sense: CTCAGCCTCCTAGC-CAAGTCC (SEQ ID NO 19); antisense: GTATTGTCCA-CATTCTCCAAC (SEQ ID NO: 20)). Fibronectin and GAPDH probes were generated as described in Example 2 Specific primers were used to amplify gremlin/IHG-2 (external sense: ATGAGCCGCACAGCCTACAC (SEQ ID NO: 21); external antisense: GTATTGTCCACATTCTC-CAAC (SEQ ID NO: 22); internal sense: GAGAGTCA-CACGTGTGAAGC (SEQ ID NO: 23); internal antisense: AGGAGGATGCAAGCACAGG (SEQ ID NO: 24), BMP-2 (external sense: CGCGGATCCTGCTTCTTAGACGGACT-GCG (SEQ ID NO: 25); external antisense: TTTGCTG-TACTAGCGACACC (SEQ ID NO: 26); internal sense: CAAGATGAACACAGCTGG (SEQ ID NO 27)), and GCT-CAGGATACTCAAGAC (SEQ ID NO: 28)). RT-PCR was carried out as reported as described in Example 3.

Figure 16:
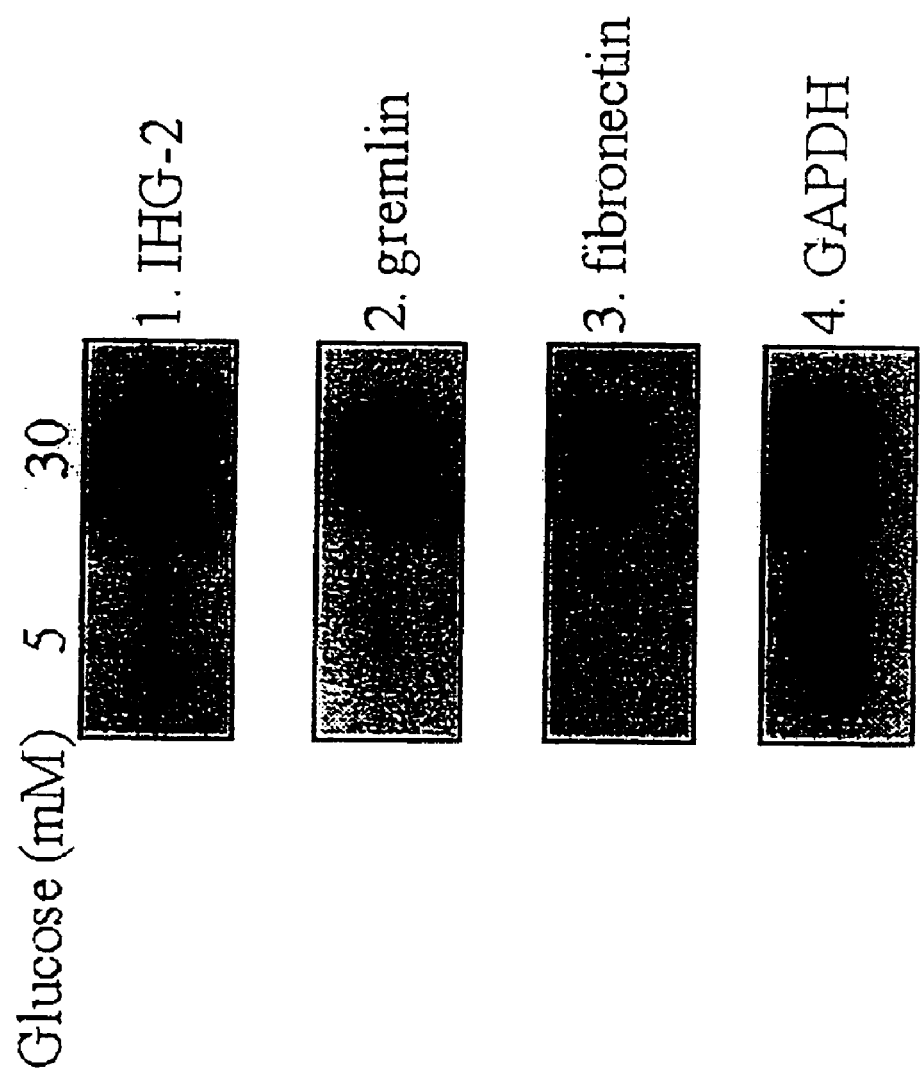
FIG. 16 is an autoradiograph of IHG-2, gremlin, fibronectin and GAPDH mRNA levels analysed by Northern Blot as described in Example 7.
Figure 17:
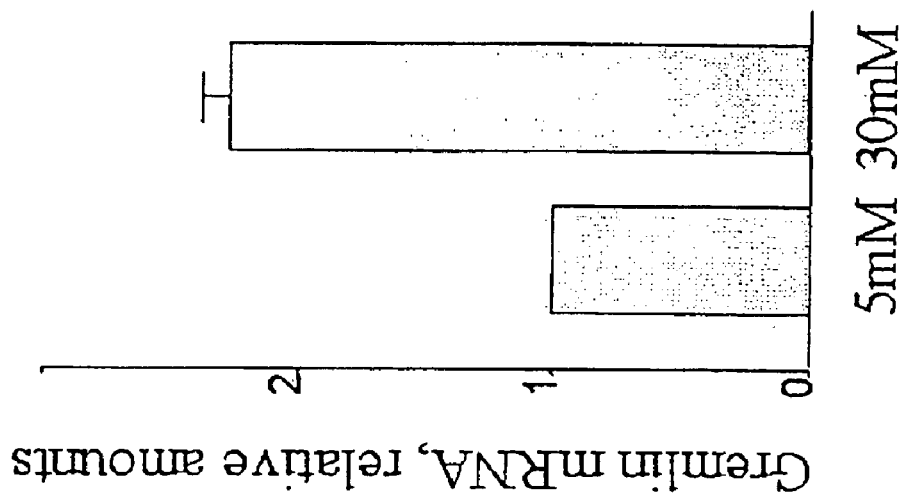
FIG. 17 is a graph of relative MRNA levels as estimated by Phosphor Imager quantification as described in Example 7.

The results are shown in FIGS. 16 and 17.

In FIGS. 16 and 17, lane 1 corresponds to the mesangial cells exposed to 5 mM glucose and lane 2 corresponds to the mesangial cells exposed to 30 mM glucose.

FIG. 16 is an autoradiograph of IHG-2 (1), gremlin (2), fibronectin (3) and GAPDH (4) mRNA levels analysed by Northern Blot. Two bands of approximately 4.4 kb and 4.6 kb were detected following hybridisation to the gremlin and IHG-2 probes.

FIG. 17 depicts relative mRNA levels as estimated by Phosphor Imager quantification. Values were normalised to GAPDH levels. The results are representative of three independent experiments.

B) Glomerular hypertension is an independent risk factor for the development of glomerulosclerosis in diabetes mellitus (Brenner, B. M., et al. (1982) *N. Engl. J. Med* 307, 652–9). To model the effects of glomerular hypertension on mesangial cell gremlin expression in the present study, mesangial cells were propagated under conditions of cyclic mechanical strain for 24 and 48 h in the Flexercell™ System For the application of mechanical cyclic stretch, primary human mesangial cells were seeded on either flexible or rigid based, elastin coated six-well plates (Flex I and Flex II plates, Flex Cell™ Int, Hillsborough, N.H., USA). Cells were grown to 90% confluency, then serum restricted in Clonetics™ Mesangial Basal Medium supplemented with 0.5% fetal calf serum. Cells cultured on flexible plates were subjected to repeated cycles of computer-controlled, vacuum-driven mechanical stretch and relaxation using the Flexercell Strain Unit FX-2000 (Flexercell™). Cells were alternately stretched and relaxed at 0.5 sec intervals (60 cycles/min) for either 24 or 48 h. The applied vacuum achieved a 17% elongation of the outer annulus of the culture plates. All experiments were carried out at 37° C. and 5% $CO_2$ in a humidified incubator.

The results were obtained from three diabetic rats, 14 weeks following onset of diabetes and from three age matched controls.

The model used perturbs mesangial cell matrix production and metabolism in a manner similar to that observed in diabetic glomerulosclerosis in vivo. Mesangial cell gremlin mRNA levels were significantly enhanced under conditions of mechanical strain, in parallel with increased fibronectin mRNA expression as shown in FIGS. 18 and 19.

Figure 18:
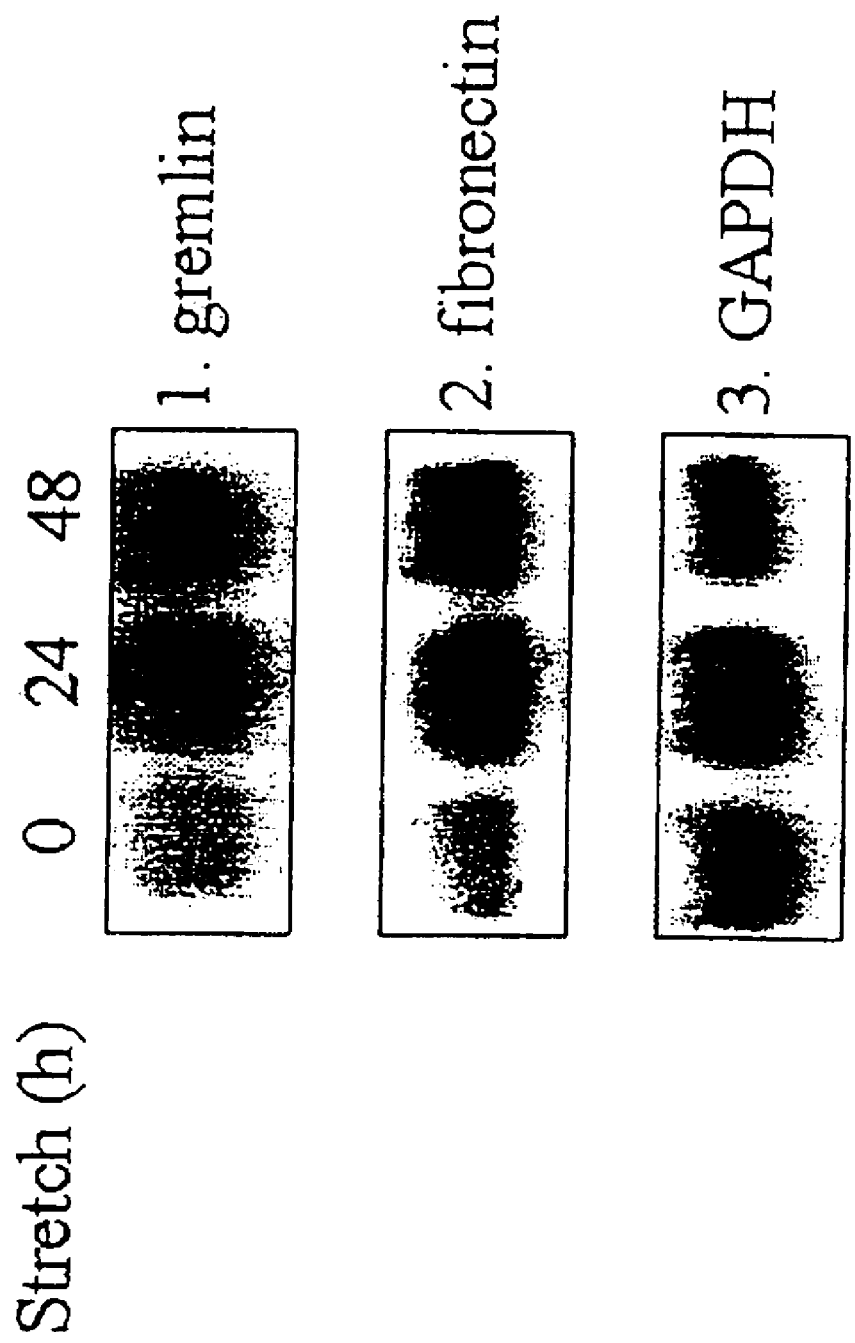
FIG. 18 is an autoradiograph of gremlin, fibronectin and GAPDH mRNA analysed by Northern Blot as described in Example 7.
Figure 19:
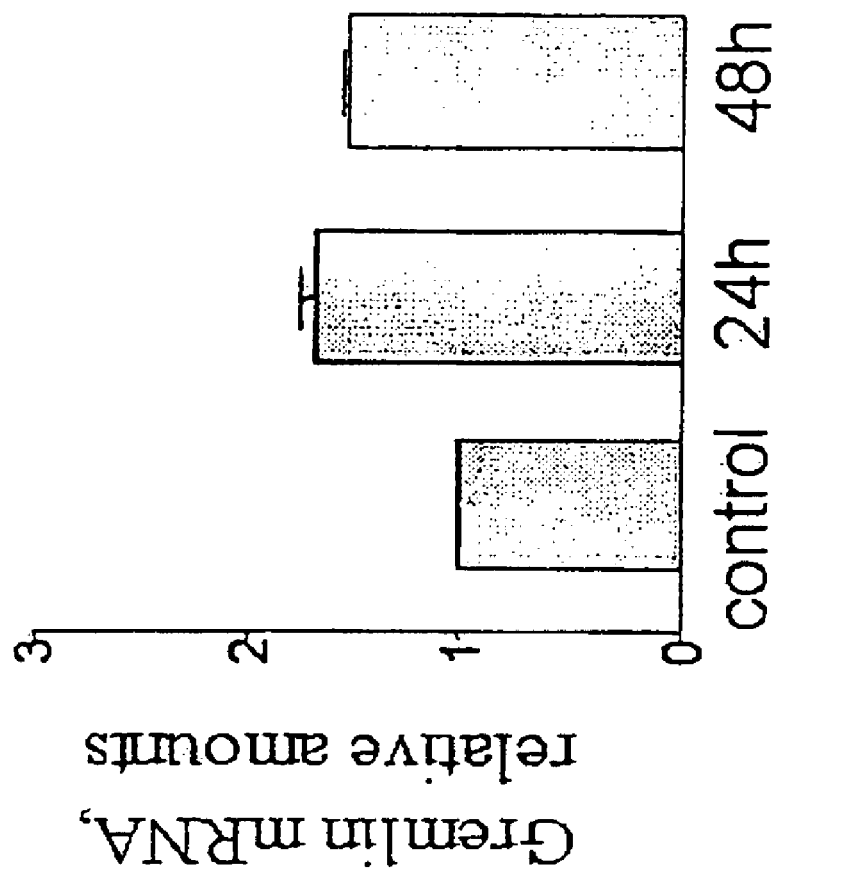
FIG. 19 is a further graph of relative mRNA levels as estimated by Phosphor Imager quantification as described in Example 7.

Referring to FIGS. 18 and 19 mesangial cells in culture were grown under static conditions (lane 1) or during exposure to cyclic stretch for 24 h (lane 2) or 48 h (lane 3) using the Flexercell™ System.

FIG. 18 is an autoradiograph of gremlin(1), fibronectin(2) and GAPDH(3) mRNA analysed by Northern Blot.

In FIG. 18 the lanes represent the following:

Lane 1: Mesangial cells grown in culture under static conditions;

Lane 2: Mesangial cells grown in culture during exposure to cyclic stretch for 24 h; and Lane 3: Mesangial cells grown in culture during exposure to cyclic stretch for 48 h.

FIG. 19 depicts relative mRNA levels as estimated by Phosphor Imager quantification. Values were normalised to GAPDH levels.

To assess gremlin expression in diabetic nephropathy in vivo, gremlin mRNA levels were measured by Northern Blot analysis with RNA isolated from the renal cortex of control rats and from diabetic rats 14 weeks after induction of diabetes mellitus by streptozotocin (STZ). In keeping with the in vitro experiments reported above, gremlin mRNA levels were increased in kidneys from diabetic rats, coincident with proteinuria and histologic evidence of diabetic nephropathy (data not shown).

Nine Male Munich-Wistar uninephrectomized rats were rendered diabetic with streptozotocin, and the RNA extracted as described in Example 3.

Figure 21:
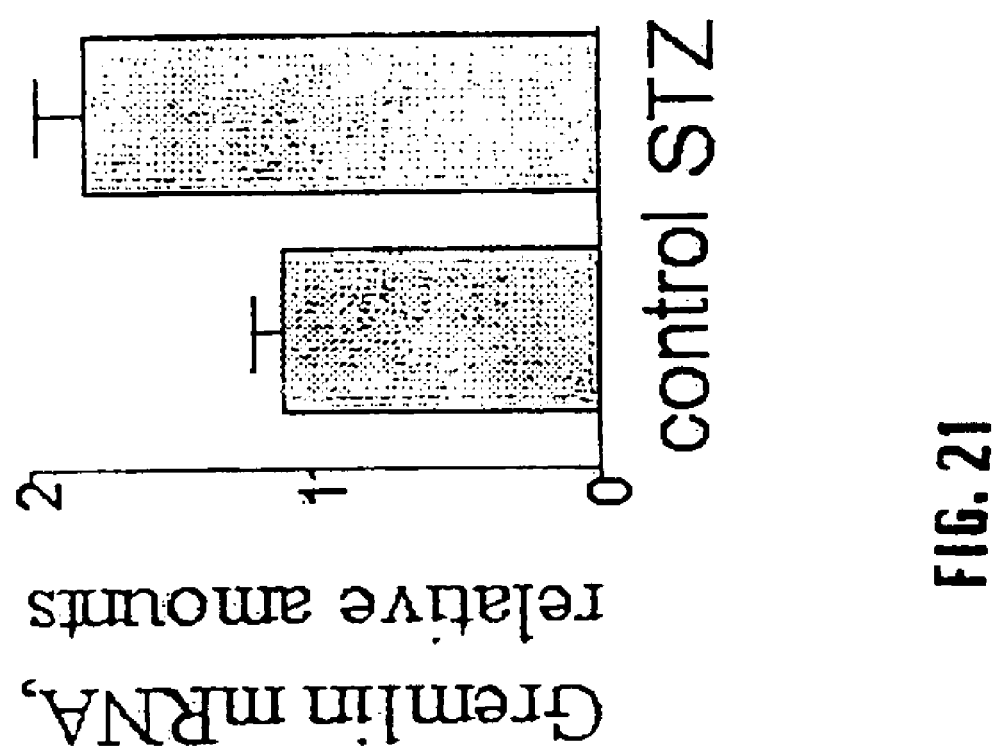
FIG. 21 is a further graph of relative mRNA levels as estimated by Phosphor Imager quantification as described in Example 7.

The results are shown in FIGS. 20 and 21, which show gremlin MRNA levels in renal cortex of STZ-diabetic rats.

FIG. 20 is an autoradiograph of gremlin mRNA levels in the kidney cortex of a STZ-diabetic rat (lane 2) and an age matched control (lane 1) analysed by Northern Blot. A band of approximately 4.4 kb was detected following hybridisation to the gremlin probe.

FIG. 21 depicts relative mRNA levels as estimated by Phosphor Imager quantification. Values were normalised to GAPDH levels.

EXAMPLE 8

Regulation of Mesangial Cell Gremlin Expression by High Glucose: Evidence for Involvement of TGF-β1

As indicated above, both high ambient glucose concentrations and cyclic mechanical strain provoke TGF-β1 production by mesangial cells in vitro and TGF-β1 appears to be a major stimulus for mesangial matrix accumulation in diabetic glomeruli in vivo. To probe the mechanism by which high glucose triggers gremlin expression, primary human mesangial cells were propagated in 5 mM or 30 mM glucose in the presence and absence of anti-TGF-β1 neutralising antibody (1 μgrml). Treatment of cultures with glucose and anti-TGF-β1 were as described in Example 1 and Example 4. respectively. To assess the role of TGF-β1 as a stimulus for gremlin expression, cells were serum restricted for 24 h in MCDB131 and 0.5% PBS and subsequently treated with 10 ng/ml TGF-β1. MCDB131 is a specialised medium for the growth of mesangial cells and is obtained from Clonetics.

Initial studies had indicated that TGF-β1 neuturalizing antibody (data not shown) blunted glucose-triggered gremlin expression and therefore the ability of TGF-β1 to alter gremlin expression was investigated. The results are shown in FIGS. 22 and 23.

The addition of exogenous human recombinant TGF-β1 (10 ng/ml, 24 h) to serum restricted (24 h) mesangial cells also augmented gremlin MRNA levels, suggesting that high glucose enhances gremlin mRNA expression, at least in part, through its ability to stimulate TGF-β1 expression. In aggregate, these observations suggest the presence of a novel autocrine loop through which TGF-β1 induces gremlin gene expression and may thereby regulate the activity of mesangial-derived BMPs as hereinafter described.

It was found that gremlin expression in response to high glucose (30 mM, 7 days) was reduced in the presence of anti-TGF-β1 antibody (data not shown). To further probe the role of TGF-β1 as a modulator of gremlin expression, mesangial cells were exposed to TGF-β1 (10 ng/ml) for 24 h (lane 2). Cells cultured in MCDB131 and 0.5% FBS for 24 h served as a control (lane 1).

Figure 22:
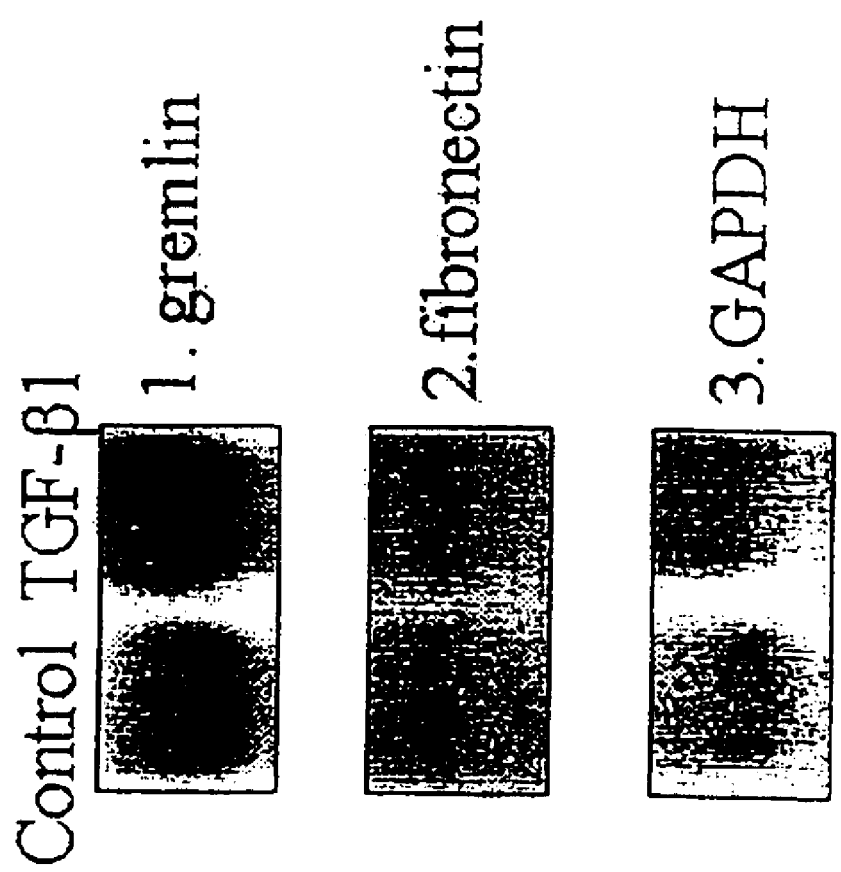
FIG. 22 is an autoradiograph of gremlin, fibronectin and GAPDH mRNA levels analysed by Northern Blot as described in Example 8.
Figure 23:
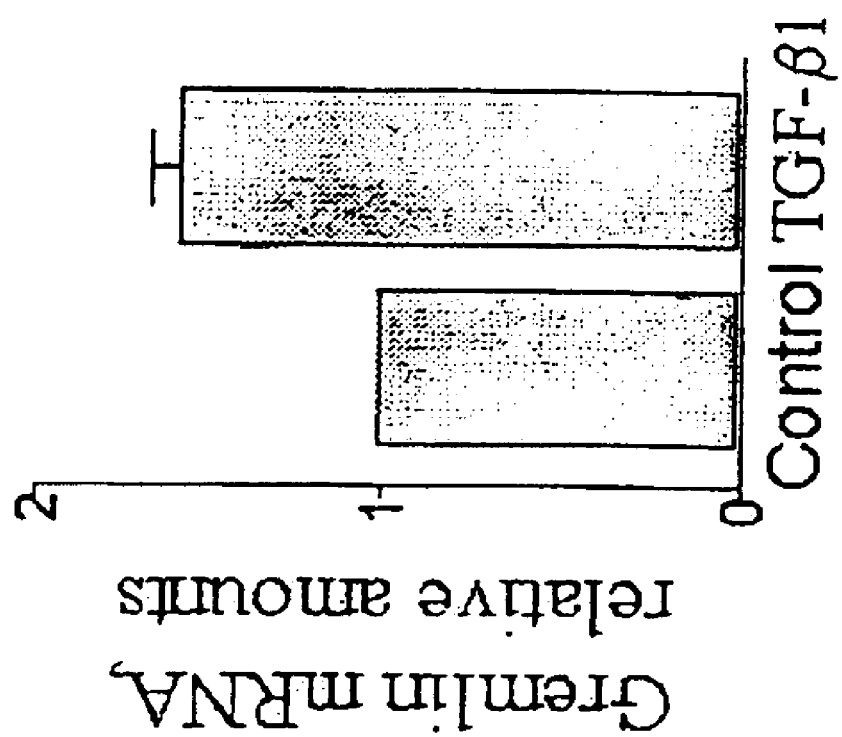
FIG. 23 is a graph of relative mRNA levels as estimated by Phosphor Imager quantification.

FIG. 22 is an autordiograph of gremlin (1), fibronectin (2) and GAPDH (3) mRNA levels analysed by Northern Blot.

FIG. 23 shows relative mRNA levels as estimated by Phosphor imager quantification. Values were normalised to GAPDH levels.

EXAMPLE 9

High Glucose Stress Induces BMP-2, but not BMP-4 Expression in Mesangial Cells

As indicated above gremlin is a putative antagonist of BMP-2 and BMP-4. Specifically, gremlin has been recently reported to form heterodimers with BMPs and thereby antagonise BMP signalling (Hsu, D. R., et al. (1998) supra). In the present study, RT-PCR was employed as an initial assessment of mesangial cell BMP expression.

As an initial assessment of the relationship between gremlin expression and BMP expression, RNA was isolated from mesangial cells grown for 7 days in either 5 mM or 30 mM glucose. Following reverse transcription with random primers, a primary PCR of the ORF of BMP-2 was performed. This product, which was undetectable on an ethidium stained agarose gel after 30 cycles, was nested to give a predicted product of 446 bp. PCR analysis with BMP-4 and GAPDH specific primers gave predicted products of 378 bp and 452 bp respectively.

FIG. 24 depicts representative reactions of 4 independent experiments. 10 μl of each PCR reaction was run on 1% ethidiun bromide stained agarose gels.

Whereas little or no BMP-2 mRNA was detected in mesangial cells propagated in 5 mM glucose, a marked induction of BMP-2 expression was observed in cells cultured in 30 mM glucose as shown in FIG. 24.

In contrast, BMP4 expression levels were relatively unchanged. Interestingly, whereas BMP-2 does not stimulate fibronectin expression in mesangial cells in vitro, BMP-2 has been recently shown to block mesangial cell proliferation triggered by epidermal growth factor and platelet-derived growth factor (Ghosh Choundhury, G., et al., (1999) *J. Biol. Chem.* 274, 10897–902; Ghosh Choudhury, G., et al., (1999) *Biochem. Biophys. Res. Commun.* 258, 490–6). Our results raise the possibility that TGF-β1 stimulated expression of gremlin may contribute to mesangial cell proliferative responses in this setting. The influence of gremlin on cell proliferation appears complex, however, and may vary markedly depending on the cell-type and proliferative stimulus. In contrast to the aforementioned potentially pro-proliferative actions, over-expression of the gremlin homologue, drm, causes apoptosis in fibroblasts by an ERK mediated pathway, while cells transformed with oncogenes such as v-mos show suppressed drm expression (Topol, L. Z., et al., (1997) *Mol. Cell. Biol.* 17, 4801–10 ). Similarly, over-expression of DAN, another cysteine knot super-family member with homology to drm/gremlin, retards fibroblast entry into S phase (Ozaki, T., et al, (1995) *Cancer Res.* 55, 895–900).

In summary, our results demonstrate that the DAN family member gremlin is induced in diabetic nephropathy in vivo and implicate both metabolic and hemodynamic stress as stimuli for gremlin expression.

The findings that high glucose-triggered gremlin expression is mimicked by addition of exogenous TGF-β1, blunted by anti-TGF-β1 neutralising antibody, and occurs in association with induction of mesangial cell BMP-2 suggests the presence of a novel autocrine loop which may limit the bioactivity of TGF-β1 superfamily members and modulate mesangial cell proliferation within the diabetic mesangium. The further elucidation of the functional interactions of the DAN family of secreted proteins, such as gremlin, with TGF-β1 superfamily members may shed light on the complex multi-pronged molecular events that perturb cell proliferation and matrix production in diabetic glomerulosclerosis.

What is claimed is:

1. A method for identifying a gene which may be involved with the presentation of diabetic nephropathy, which method comprises culturing mesangial cells in a medium in the presence of exogenously added transforming growth factor β1 (TGF-β1) and a concentration of glucose sufficient to induce differential expression of a gene susceptible to such differential expression;

and identifying the gene so induced by suppression subtractive hybridization.

2. A method according to claim 1, wherein the mesangial cells are cultured in the presence of a concentration of glucose sufficient to induce up-regulation of a gene susceptible to such up-regulation.

3. A method according to claim 1, wherein the concentration of glucose is greater than 5 mM.

4. A method according to claim 1, wherein the mesangial cells are subjected to mechanical strain.

5. A method for identifying a gene which may be involved with the presentation of diabetic nephropathy, which method comprises culturing mesangial cells in a medium in the presence of transforming growth factor β1 (TGF-β1) and a concentration of glucose sufficient to induce differential expression of a gene susceptible to such differential expression;

and identifying the gene so induced by suppression subtractive hybridization, wherein the possibility of differential expression due to hyperosmolarity is excluded.

6. A method according to claim 1, wherein the gene so differently expressed is a gene of SEQ ID NO:1.

7. An isolated nucleic acid comprising the sequence of SEQ ID NO:1.

* * * * *